United States Patent
Grohowski, Jr.

(10) Patent No.: US 9,370,609 B2
(45) Date of Patent: Jun. 21, 2016

(54) HIGH STRENGTH INJECTION MOLDED ORTHOPEDIC DEVICES

(71) Applicant: Praxis Powder Technology, Inc., Queensbury, NY (US)

(72) Inventor: Joseph A. Grohowski, Jr., Glen Falls, NY (US)

(73) Assignee: Praxis Powder Technology, Inc., Queensbury, NY (US)

(*) Notice: Subject to any disclaimer, the term of this patent is extended or adjusted under 35 U.S.C. 154(b) by 0 days.

(21) Appl. No.: 14/150,686

(22) Filed: Jan. 8, 2014

(65) Prior Publication Data

US 2014/0195001 A1 Jul. 10, 2014

Related U.S. Application Data

(60) Provisional application No. 61/750,225, filed on Jan. 8, 2013.

(51) Int. Cl.
| | |
|---|---|
| *B22F 5/00* | (2006.01) |
| *A61L 27/56* | (2006.01) |
| *A61L 27/06* | (2006.01) |
| *A61L 27/50* | (2006.01) |
| *B22F 3/11* | (2006.01) |
| *B22F 3/22* | (2006.01) |
| *B22F 7/06* | (2006.01) |

(52) U.S. Cl.
CPC ............ *A61L 27/56* (2013.01); *A61L 27/06* (2013.01); *A61L 27/50* (2013.01); *B22F 3/1137* (2013.01); *B22F 3/225* (2013.01); *B22F 5/00* (2013.01); *B22F 7/06* (2013.01); *A61L 2430/02* (2013.01); *B22F 2999/00* (2013.01); *Y02P 10/295* (2015.11)

(58) Field of Classification Search
CPC ...................................................... B22F 5/10
See application file for complete search history.

(56) References Cited

U.S. PATENT DOCUMENTS

| | | |
|---|---|---|
| 2,672,415 A | 3/1954 | Balke |
| 3,138,857 A | 6/1964 | Kuchek |
| 3,362,818 A | 1/1968 | Schwarzkopf et al. |
| 3,802,878 A | 4/1974 | Lindstrom |
| 3,852,045 A | 12/1974 | Wheeler et al. |
| 4,588,540 A | 5/1986 | Kiefer et al. |

(Continued)

FOREIGN PATENT DOCUMENTS

| | | |
|---|---|---|
| WO | 01/19556 A1 | 3/2001 |
| WO | 2004/039748 A1 | 5/2004 |
| WO | 2010/045255 A1 | 4/2010 |

OTHER PUBLICATIONS

International Search Report and Written Opinion received for PCT Patent Application No. PCT/US2014/10749, mailed on May 2, 2014, 12 pages.

(Continued)

*Primary Examiner* — George Wyszomierski
*Assistant Examiner* — Ngoclan T Mai
(74) *Attorney, Agent, or Firm* — Charney IP Law LLC

(57) ABSTRACT

High strength implantable devices having complex surfaces are injection molded from powder metal wherein the surface is defined by a monolithic insert made by additive manufacturing. The insert defines the surface texture of the device and may also include a portion to form an ingrowth texture and a portion to form a substrate interface texture. The tensile bond strength of the texture is 20 Mega Pascal or greater.

19 Claims, 34 Drawing Sheets

(56) References Cited

U.S. PATENT DOCUMENTS

| | | | |
|---|---|---|---|
| 4,765,950 A | | 8/1988 | Johnson |
| 5,641,920 A | | 6/1997 | Hens et al. |
| 5,658,334 A | | 8/1997 | Caldarise et al. |
| 5,678,162 A | * | 10/1997 | Barlow et al. .................. 419/2 |
| 5,976,457 A | * | 11/1999 | Amaya et al. .................. 419/36 |
| 6,008,281 A | | 12/1999 | Yang et al. |
| 6,022,509 A | | 2/2000 | Matthews et al. |
| 6,174,493 B1 | | 1/2001 | Asbury |
| 6,582,470 B1 | | 6/2003 | Lee et al. |
| 6,592,787 B2 | | 7/2003 | Pickrell et al. |
| 6,660,224 B2 | | 12/2003 | Lefebvre et al. |
| 6,846,862 B2 | | 1/2005 | Schofalvi et al. |
| 6,994,727 B2 | | 2/2006 | Khandkar et al. |
| 7,263,159 B2 | | 8/2007 | Russell |
| 7,303,583 B1 | | 12/2007 | Schar et al. |
| 7,674,426 B2 | | 3/2010 | Grohowski, Jr. |
| 8,500,843 B2 | | 8/2013 | Grohowski |
| 2002/0086039 A1 | | 7/2002 | Lee et al. |
| 2002/0151985 A1 | | 10/2002 | Kuberasampath et al. |
| 2002/0153348 A1 | | 10/2002 | Say et al. |
| 2002/0173850 A1 | | 11/2002 | Brodke et al. |
| 2003/0009225 A1 | | 1/2003 | Khandkar et al. |
| 2003/0044301 A1 | | 3/2003 | Lefebvre et al. |
| 2003/0075013 A1 | | 4/2003 | Grohowski |
| 2003/0153981 A1 | | 8/2003 | Wang et al. |
| 2004/0072010 A1 | | 4/2004 | Date et al. |
| 2005/0049706 A1 | | 3/2005 | Brodke et al. |
| 2005/0177238 A1 | | 8/2005 | Khandkar et al. |
| 2005/0207929 A1 | | 9/2005 | Yamada |
| 2005/0271694 A1 | | 12/2005 | Mansouri et al. |
| 2006/0002810 A1 | | 1/2006 | Grohowski, Jr. |
| 2006/0003179 A1 | | 1/2006 | Wang et al. |
| 2007/0043442 A1 | | 2/2007 | Abernathie et al. |
| 2007/0191946 A1 | | 8/2007 | Heinz et al. |
| 2007/0233247 A1 | | 10/2007 | Schwab |
| 2008/0109081 A1 | | 5/2008 | Bao et al. |
| 2010/0094420 A1 | | 4/2010 | Grohowski, Jr. |
| 2010/0094426 A1 | | 4/2010 | Grohowski, Jr. et al. |
| 2010/0180724 A1 | | 7/2010 | Grohowski, Jr. |
| 2010/0319183 A1 | * | 12/2010 | Hulseman et al. ........... 29/592.1 |
| 2011/0266724 A1 | * | 11/2011 | Hulseman et al. ............ 264/603 |
| 2012/0065739 A1 | | 3/2012 | Grohowski, Jr. |
| 2012/0193841 A1 | * | 8/2012 | Wang et al. .................. 264/645 |

OTHER PUBLICATIONS

International Search Report and Written Opinion received for PCT Patent Application No. PCT/US2005/23118, mailed on Oct. 24, 2005, 8 pages.

International Search Report and Written Opinion received for PCT Patent Application No. PCT/US2007/13416, mailed on Nov. 21, 2007, 6 pages.

International Search Report and Written Opinion received for PCT Patent Application No. PCT/US2009/60545, mailed on Dec. 14, 2009, 13 pages.

Extended European Search Report received for EP Patent Application No. 05763915, mailed on Jun. 14, 2010, 9 pages.

Hens, Karl F., "Thermat Expands Precision PIM Operation", Metal Powder Report, MPR Publishing, vol. 53, No. 6, Jun. 1998, 3 pages.

Laptev et al., "Study of Production Route for Titanium Parts Combining Very High Porosity and Complex Shape", Powder Metallurgy, Maney Publishing, vol. 47, No. 1, 2004, pp. 85-92.

* cited by examiner 301         302

304
303

1101    1102

17a

2001

2002

152    151

HIGH STRENGTH INJECTION MOLDED ORTHOPEDIC DEVICES

This application claims the benefit of U.S. Provisional Application No. 61/750,225 filed Jan. 8, 2013.

BACKGROUND OF THE INVENTION

This invention relates to orthopedic and prosthetic implantable devices adapted for bone ingrowth and high strength, as well as using metal injection molding with sacrificial monolithic inserts that define the surface of at least a portion of the devices.

In the field of orthopedic devices and prostheses, coatings have been used to provide an ingrowth medium and texture to enable initial and long-term fixation of the devices to the bone. These implantable devices are generally bone prostheses and are known to include components of artificial joints, such as hips, knees, elbows and shoulders. The strength of coatings on such implants is an important consideration for short term and long term fixation to the bone.

Known methods of manufacturing coatings for implants include formation by foaming, plasma spraying, diffusion bonding or sintering of powders, depositing a material upon a substrate, use of vaporizing materials, and chemical and plasma etching. Metal injection molding has found only limited application, if any, in the manufacture of implantable devices for many reasons, including the complexities of the coating surface and ingrowth geometries, as well as the strength requirements of the devices. The fact that a molded part has to release from the mold limits the geometries of the surface. If the molded implant has an undercut, it cannot be simply separated from the mold.

It is often desirable to have features on an orthopedic or prosthetic device such as complex textures, undercuts, porosities, cavities, and other texture geometries that would not release from a mold if the device is manufactured by metal injection molding. These surfaces are intended to offer initial fixation, an ingrowth surface, and other properties desirable for implants.

Texturing the mold used for metal injection molding can achieve a roughened surface on a molded implant. The mold surface would be created as a negative of the desired texture, so as to impart the positive of the desired texture to the article during molding. Applying this methodology to more complex shapes or textures has fundamental challenges.

A complex shape or surface would include sections that have undercuts, undercut texture, internal porosity and details or elements obscured from the external surface. As such, a complex surface would not release from a mold due to its geometry.

While it may be possible to apply a simple texture to a flat surface in a mold, it is often desired to apply texture continuously around the perimeter or circumference of a part such as hip stem or acetabular cup used as an implant. Depending on the nature of the desired geometry, mold texturing has significant limitations for the nature of the textured surface imparted on the device. For example, texture around the circumference of an implant will create internal features that prevent the molded part from releasing from the mold. In some cases this can be partially addressed with complicated tooling, but the geometry of the ingrowth surface is still limited.

Even on flat surfaces, mold texturing can only create surfaces that can be released from the mold. Again, this limits the complexity of the textured portion. However, a textured portion having a complex geometry is important because it allows the surface to have "grippiness" in multiple directions.

Expendable or sacrificial inserts have been used in the mold to create tooling surfaces that form a surface geometry. Such insert can then be removed post-molding via dissolution, decomposition or other methods. However, there remains a challenge of creating the insert with appropriate complex negative texture since undercuts and other complex geometries need to be formed in the insert. Devices molded with insert fail to be able to define the entire complex character of surface and ingrowth region of the device. Moreover, the strength requirements of implants limit the complexities of such surfaces as stress concentrators form during injection molding that limit the ultimate performance of the device.

An insert for metal injection molding of a textured portion must have the negative geometry of the desired textured portion. Due to the strength requirements and complexities of implant devices, the textured portion frequently cannot be created in the insert by traditional manufacturing routes. For example, machining is a line-of-sight, subtractive manufacturing process that cannot create the complexities of a fixation texture, such as undercuts, internal cavities for ingrowth, or the substrate interfaces on the same insert. The ingrowth medium and substrate interface are obscured from the machining tool by both the ingrowth medium and the fixation texture.

Furthermore, porous coatings applied to implantable devices tend to yield reduced fatigue strength resulting from stress concentrations that arise from the interface between the coating and the dense substrate. The addition of osseo-integration surface coatings to implantable bodies diminishes the fatigue strength due to the surface interruptions at the interface between the ingrowth medium and the dense substrate. These interruptions create stress concentrations that in turn can serve as fracture initiation sites, significantly reducing the fatigue life of the device. Unfortunately, titanium, the preferred material for device bodies due to its biocompatibility, is especially vulnerable to fatigue life reduction due to perturbations on the surface. Stress concentrations at the substrate interface are a common problem with device coatings.

Additionally, the metal injection molding of titanium for implantable device surfaces using inserts brings with it several unique challenges relative to conventional metal injection molding. The issue of primary concern is contamination due to inadequate insert removal or reaction of the insert material with the titanium powder or binder during processing leading to reduced tensile bond strength of the device.

There remains a need to create a high strength implant device by metal injection molding that is at least partially porous. In addition, a device having a specified surface texture for an injection molded article while having high tensile strength and appropriate fatigue performance is sought. It would be desirable, to have a method of tailoring textured portions, including undercuts, porosity, surface curvature, and other features for injection molded implants.

BRIEF SUMMARY OF THE INVENTION

This invention provides an implantable device by manufactured by metal injection molding having a surface texture, and ingrowth medium and a substrate interface with high tensile bond strength of the texture.

In a further aspect, this invention provides a monolithic mold insert for metal injection molding and affords a process of forming a monolithic mold insert for metal injection molding via additive manufacturing, placing the mold insert for metal injection molding in an injection molding tool and molding titanium metal injection feedstock directly against the negative, and debinding and sintering the article to create a dense metal part.

In still a further aspect, this invention allows for the forming of high strength textured implantable devices where the implant is formed from powder metal.

In yet another aspect, this invention provides an implantable device that has a textured portion and a dense portion formed from differing metal powders.

This invention further provides methods of manufacturing a high strength textured implantable device where the textured portion and the dense portion constitute an undifferentiated whole.

BRIEF DESCRIPTION OF THE SEVERAL VIEWS OF DRAWINGS

For a fuller understanding of the invention, reference is made to the following descriptions taken in conjunction with the accompanying drawings in which.

Figure 8:
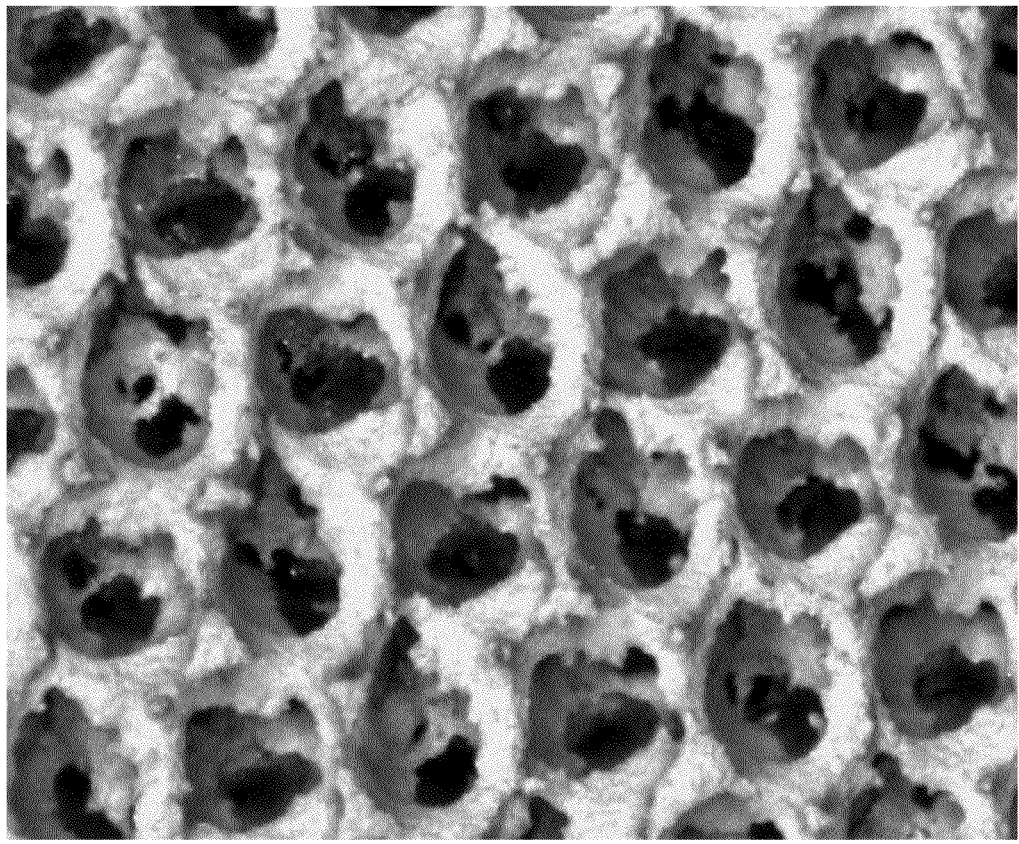
Figure 8A:
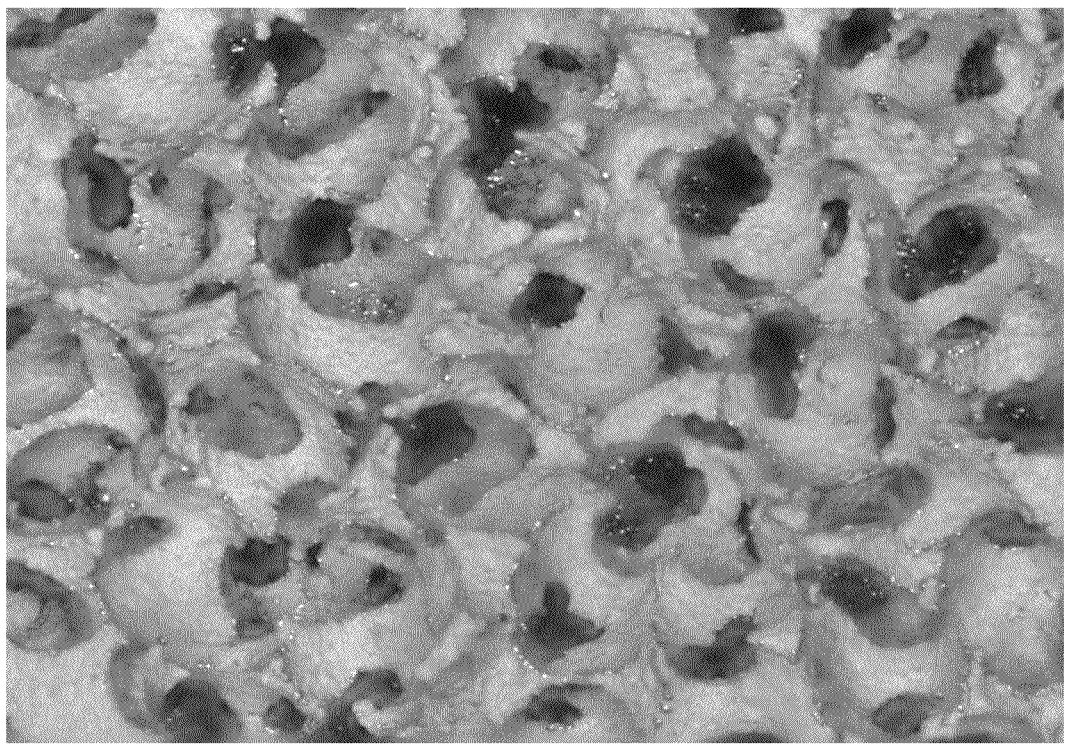
Figure 8B:
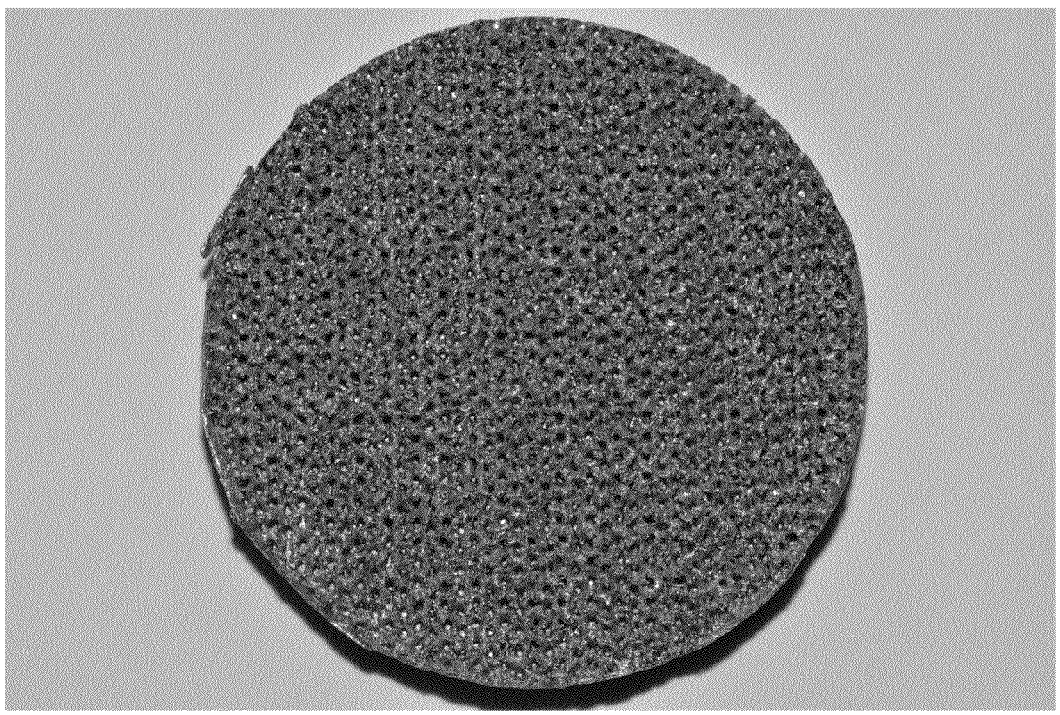
Figure 9:
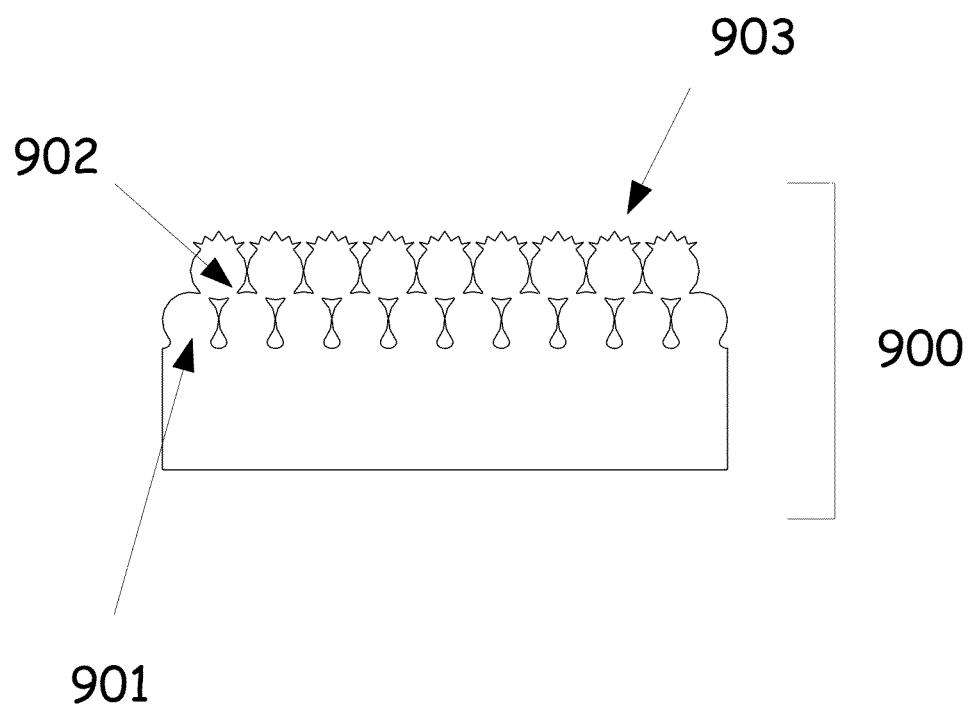

FIGS. 8, 8a, and 8b show the surface of a device according to an embodiment of the present invention FIG. 9 illustrates a schematic cross-section of a beaded surface of a textured portion of an implantable device including a fixation region according to the present invention.

Figure 10:
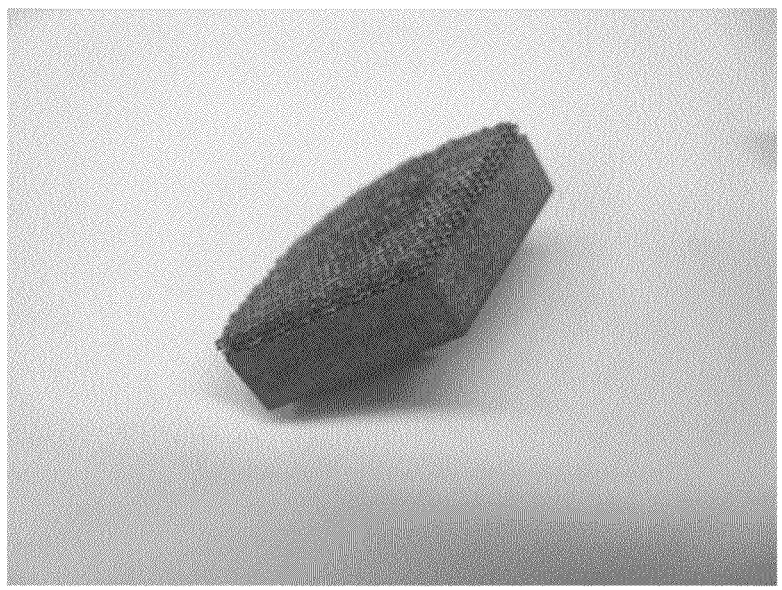
Figure 10A:
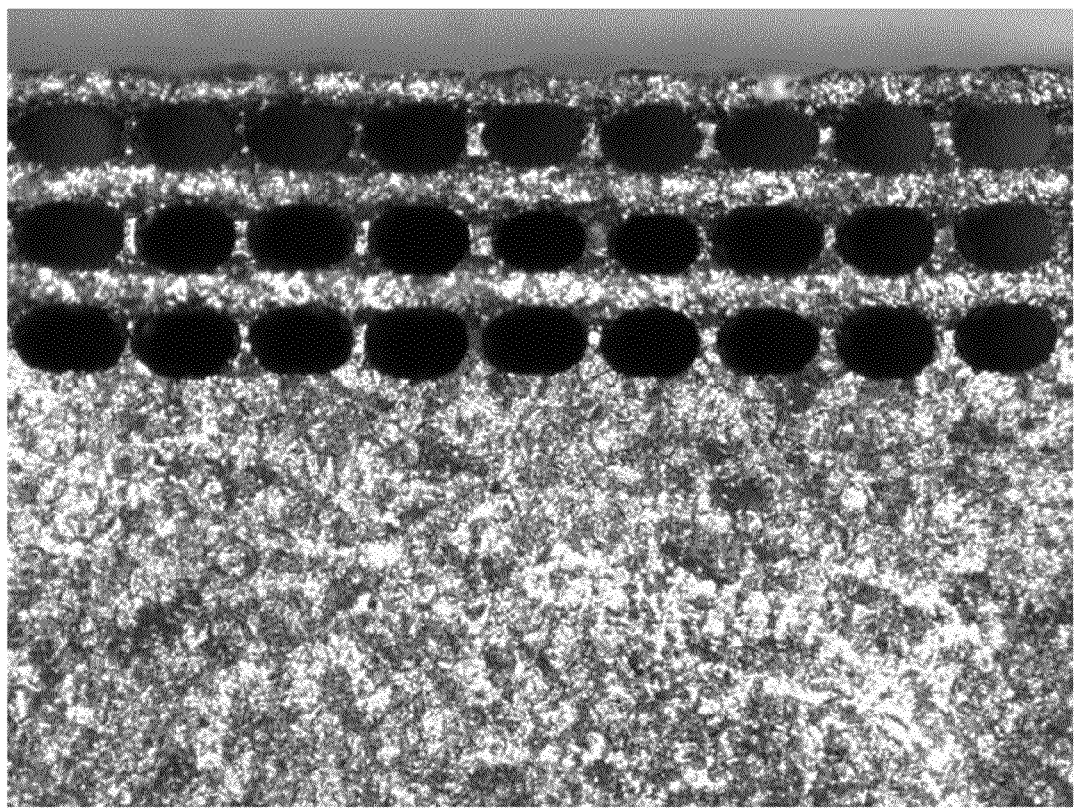

FIGS. 10 and 10a show an injection molded article including the textured portion and the dense portion.

Figure 11:
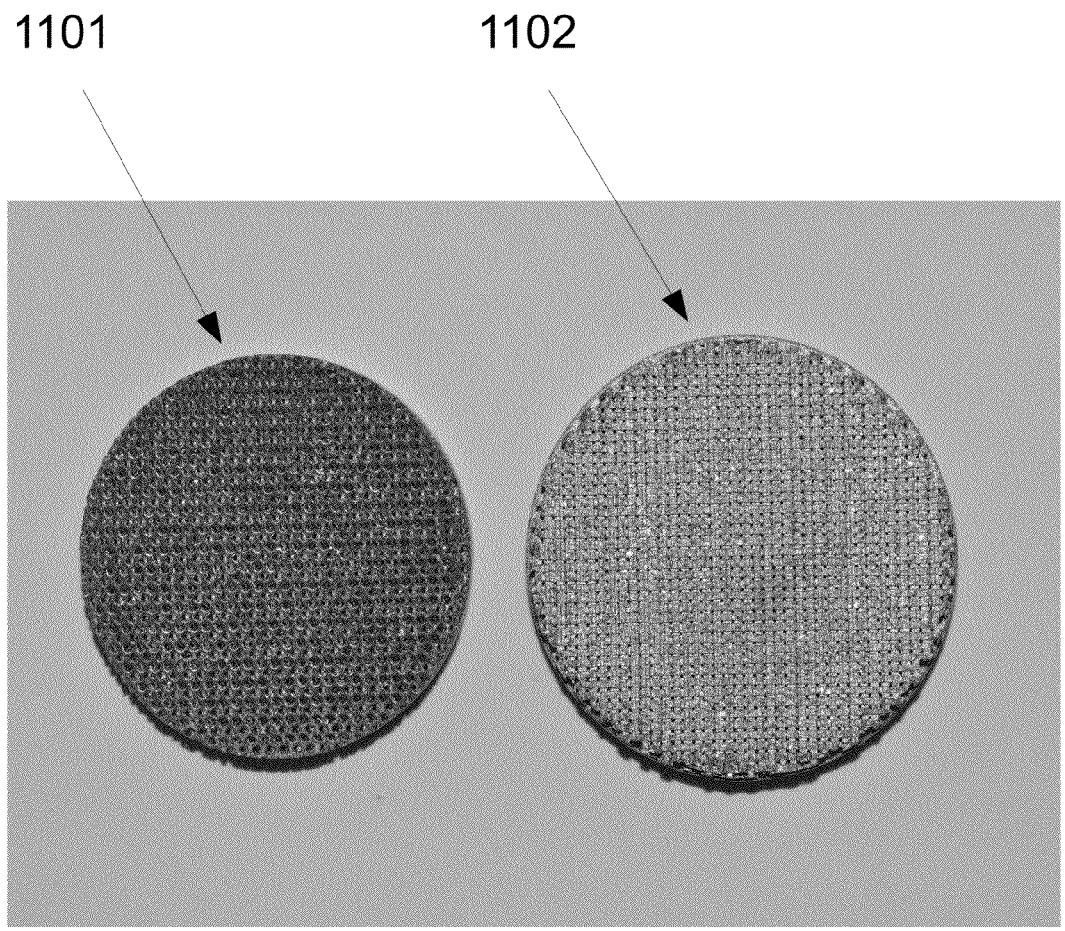

FIG. 11 depicts various porous portions according to embodiments of the invention.

Figure 12:
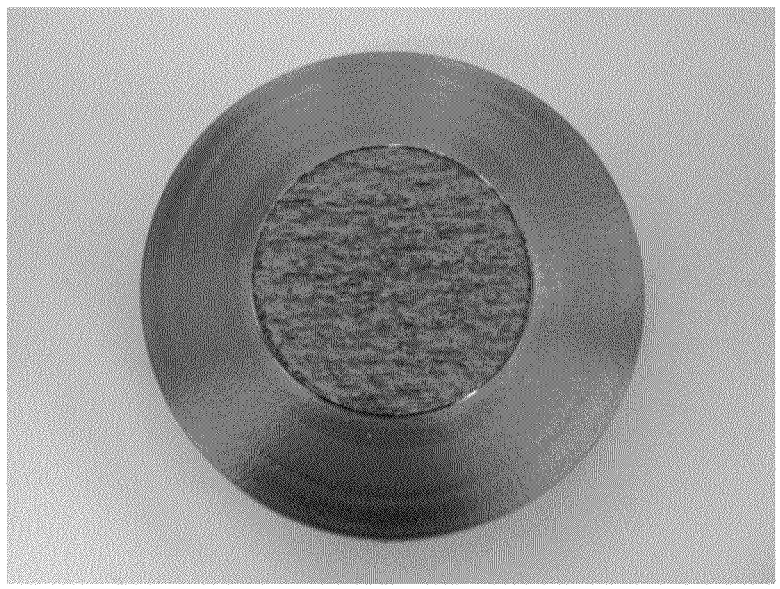

FIG. 12 depicts a sample of an device surface texture according to an embodiment of the present invention.

Figure 13:
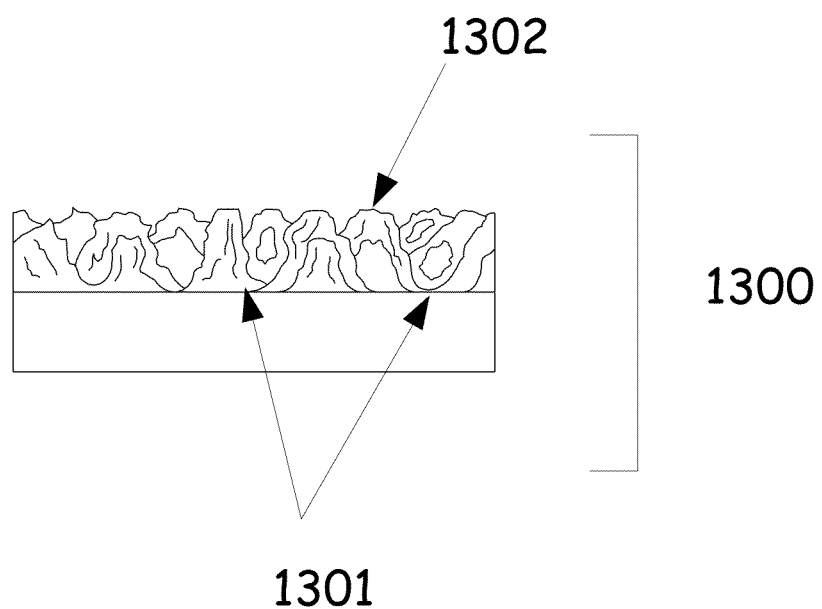

FIG. 13 is a schematic illustration of a textured interface with reduced stress concentrators.

Figure 14:
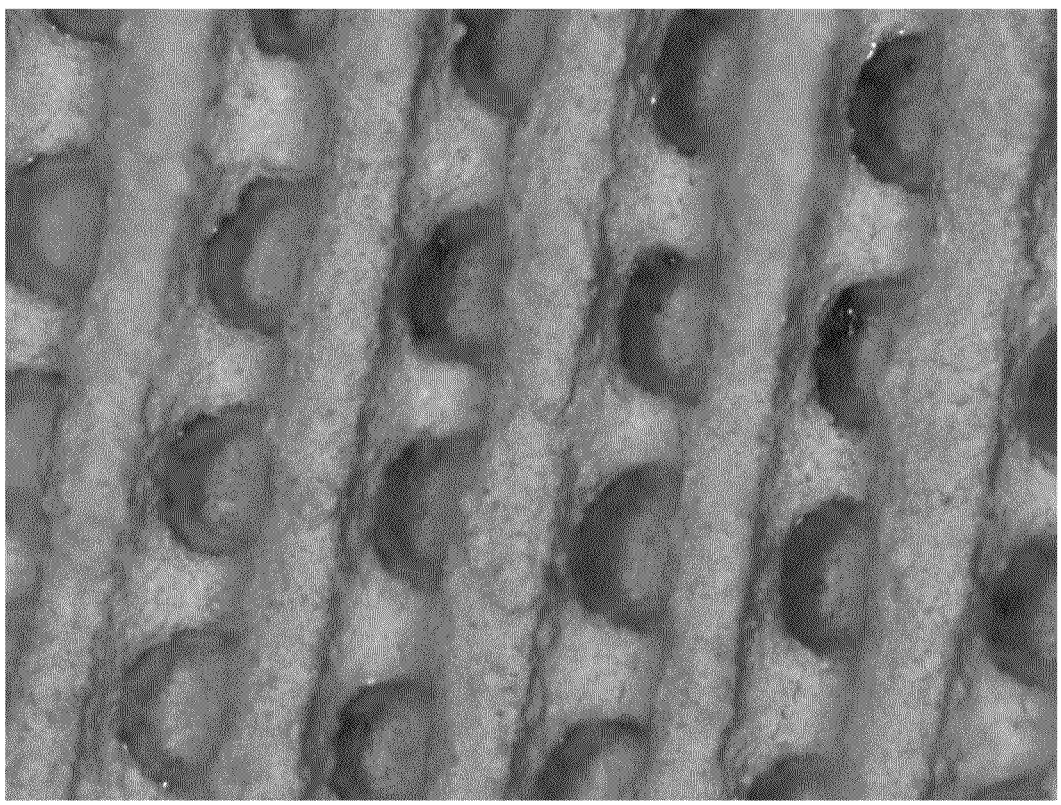

FIG. 14 shows a surface having an interlocking layer.

Figure 15:
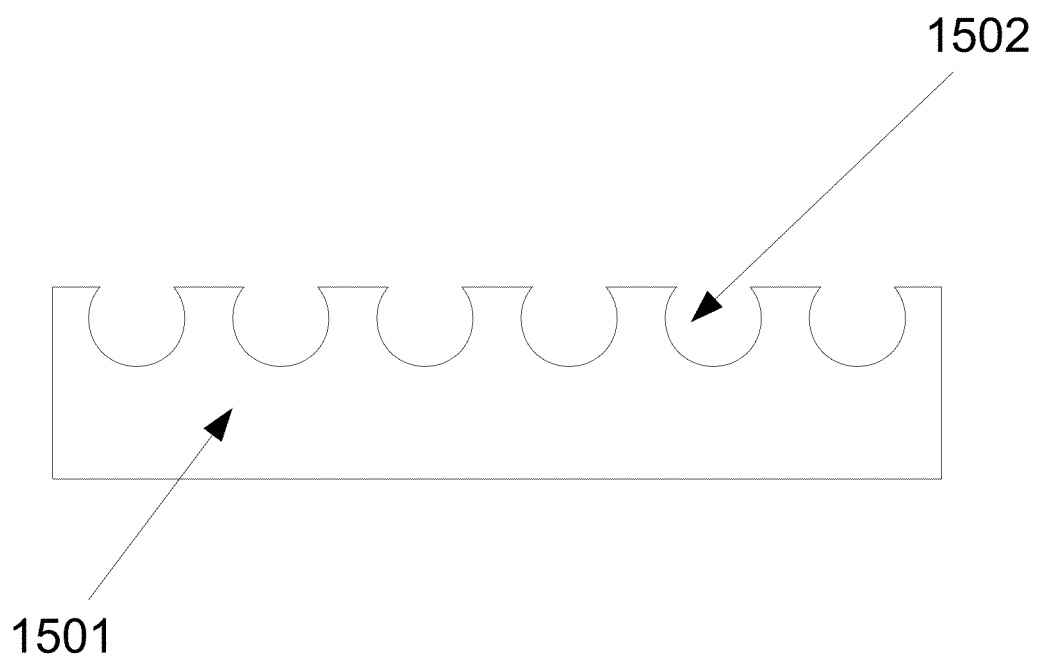

FIG. 15 is a schematic example of one embodiment of a surface having a layer with undercuts.

Figure 16:
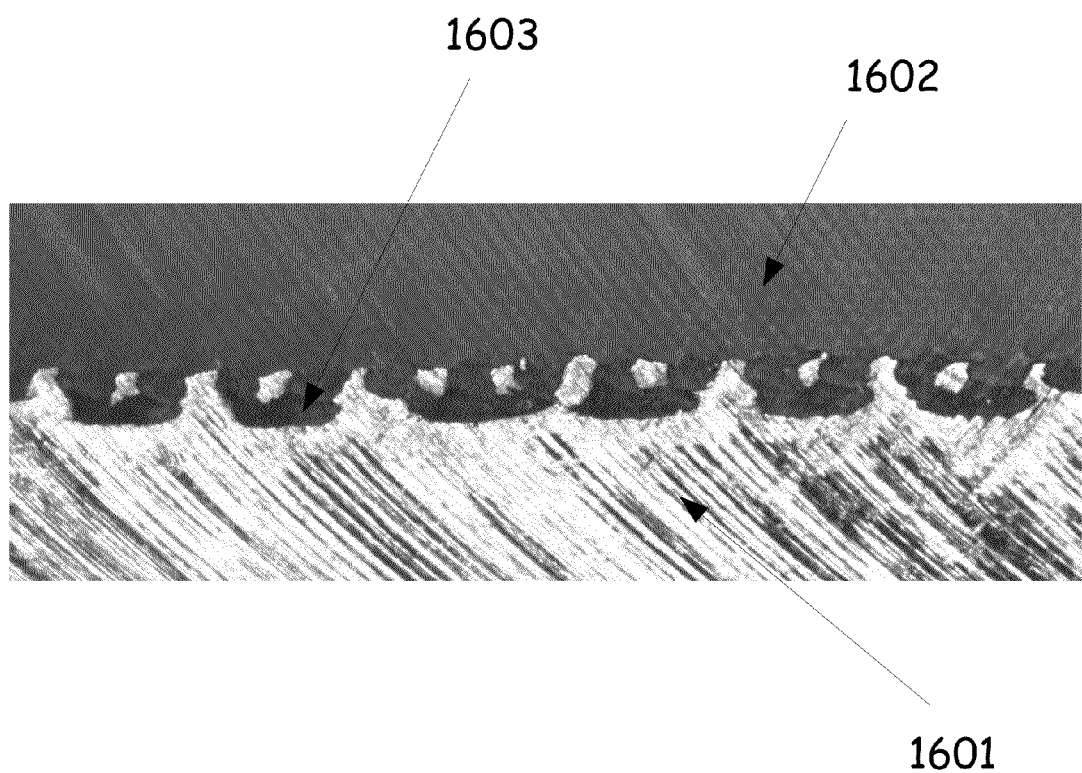

FIG. 16 shows a cross section of a polymer material penetrating an interlocking surface on a device according to the present invention.

Figure 17:
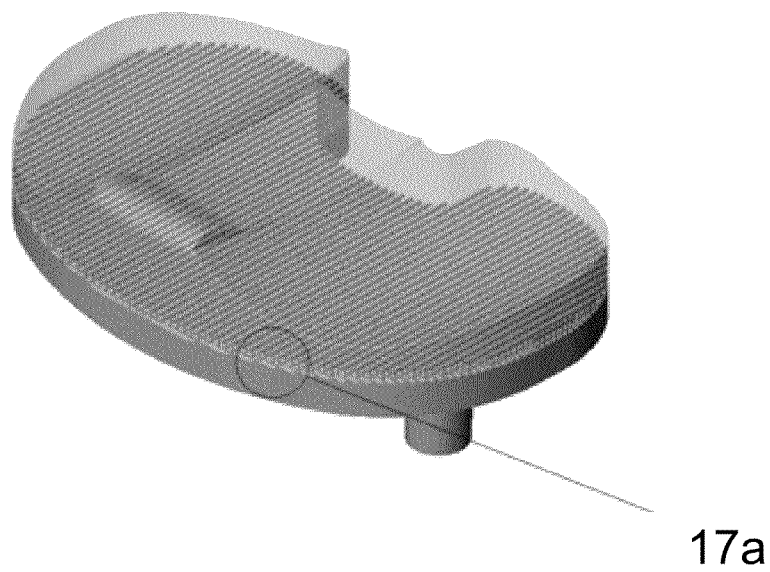
Figure 17A:
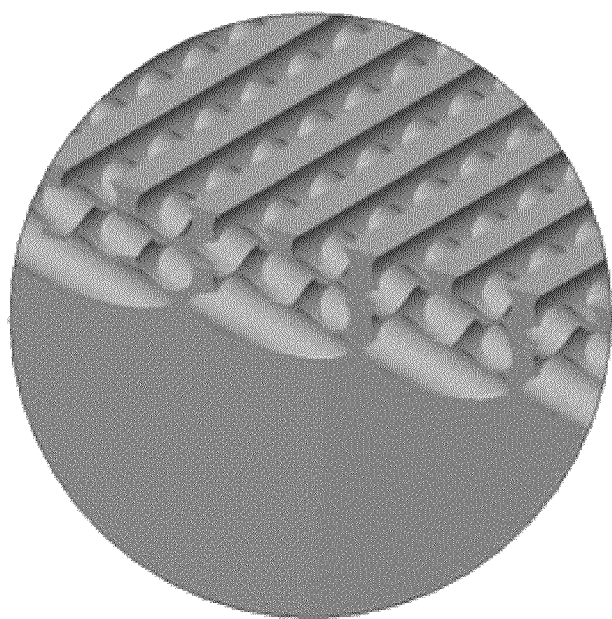

FIG. 17 and FIG. 17a show schematics of an implantable device having an engineered surface.

Figure 18:
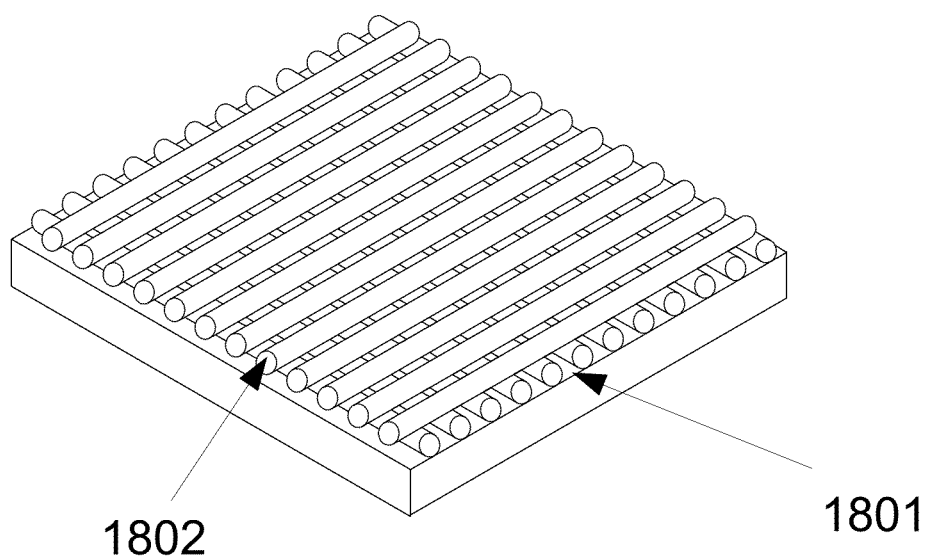

FIG. 18 shows a schematic of a monolithic sacrificial insert according to one embodiment of the invention.

Figure 19:
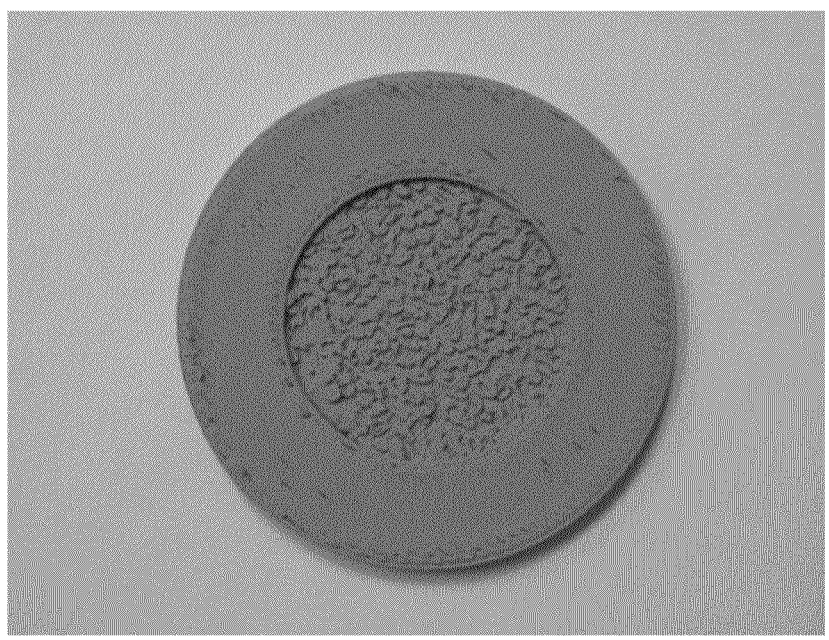
Figure 19A:
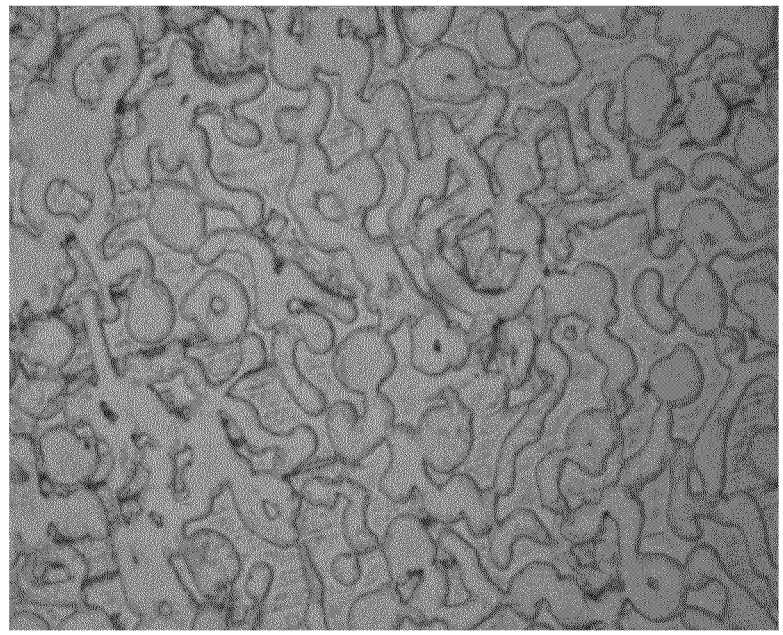

FIGS. 19 and 19a depict an insert surface used to create surface texture.

Figure 20:
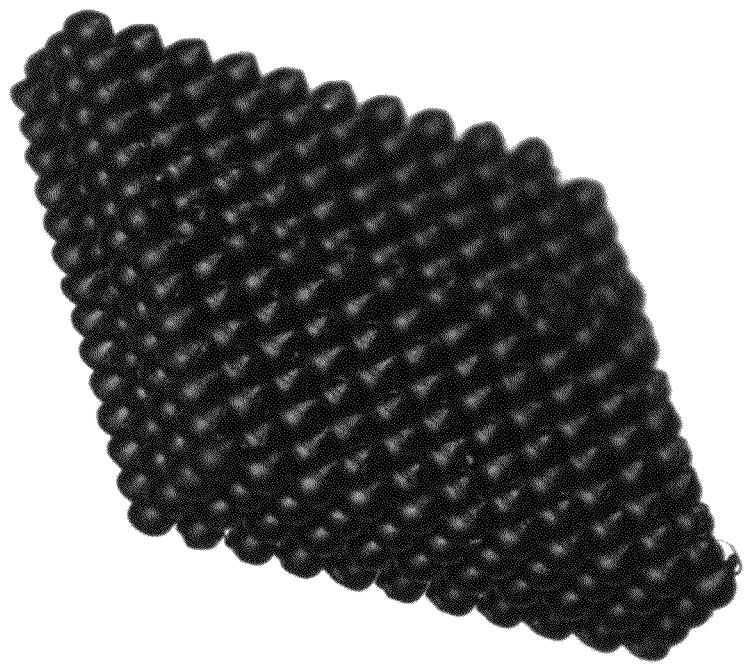
Figure 20A:
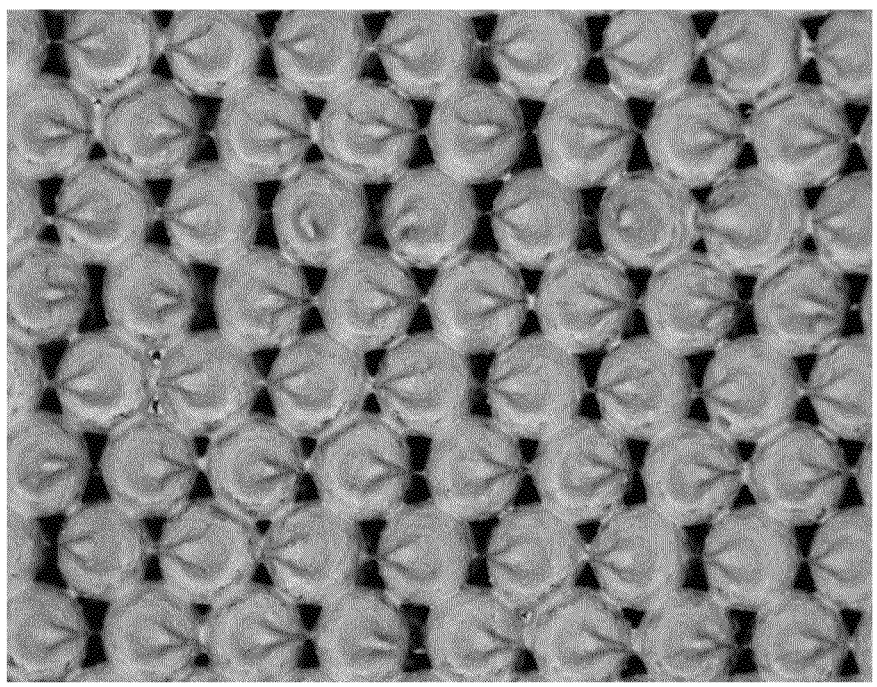
Figure 20B:
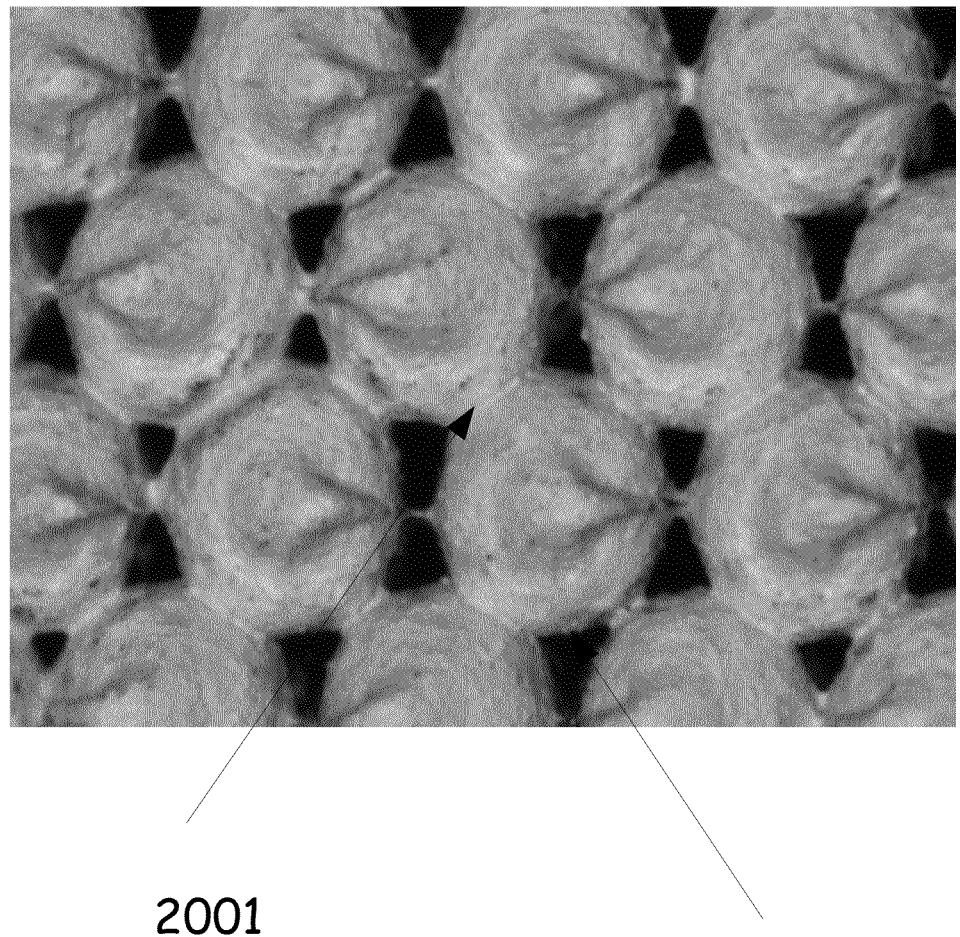

FIGS. 20, 20a, and 20b depict a monolithic insert for forming an embodiment of an ingrowth surface in an implantable device.

Figure 21:
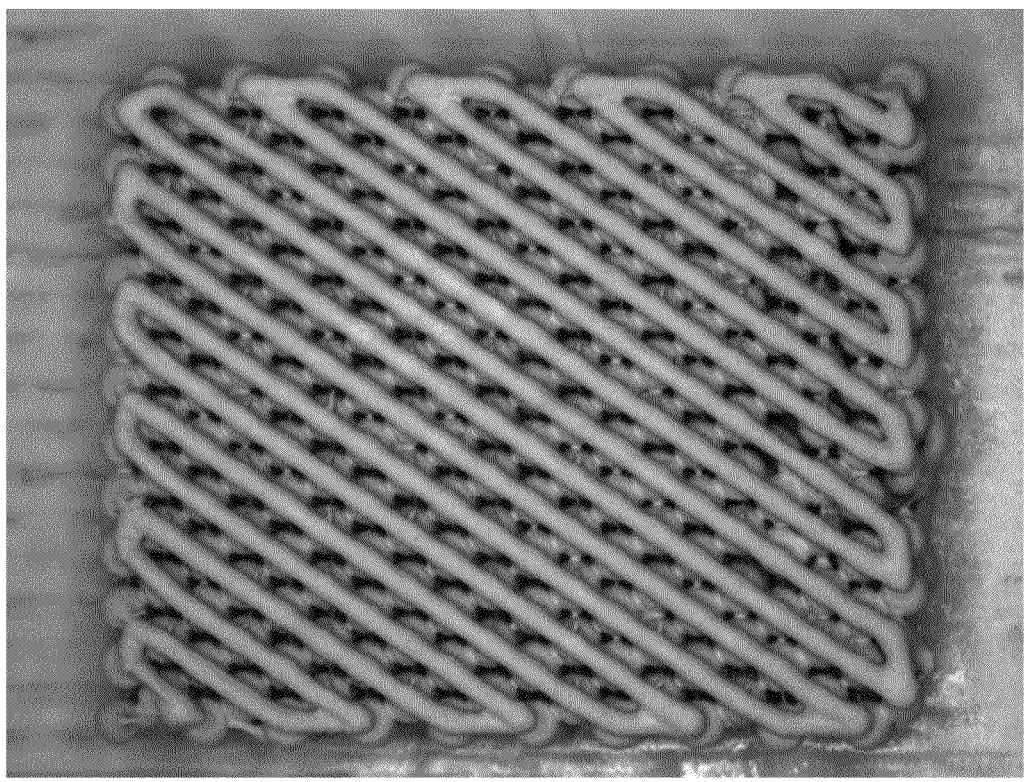
Figure 21A:
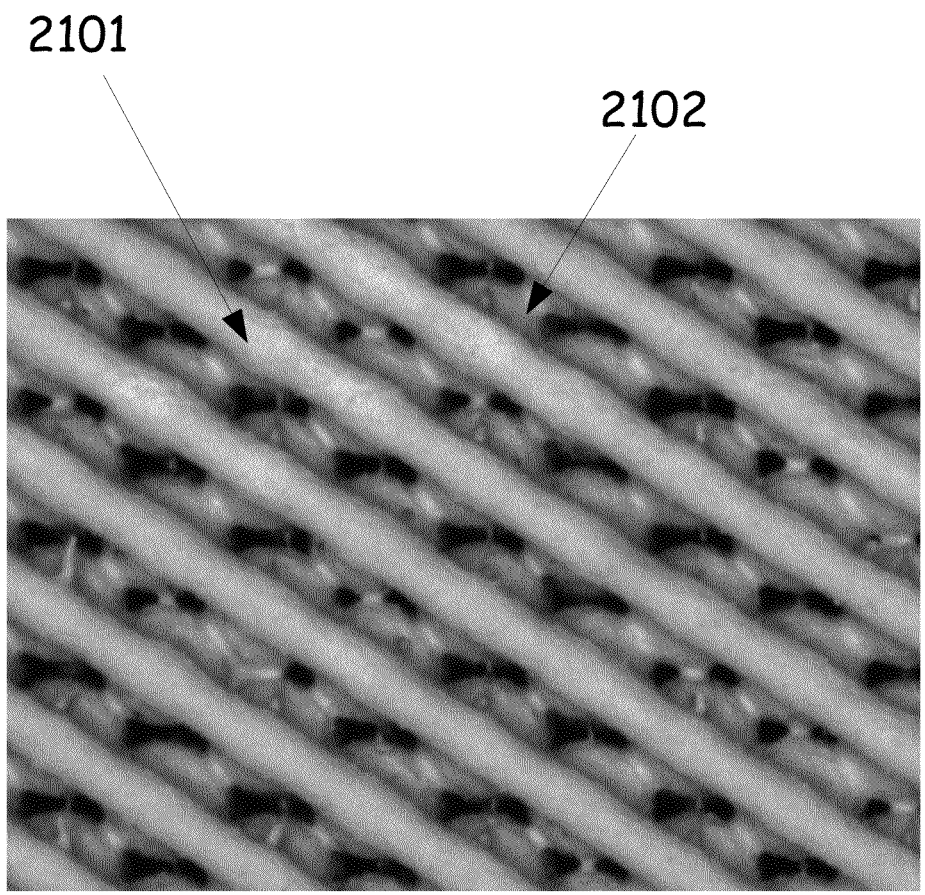

FIGS. 21 and 21a depict a monolithic insert for forming an embodiment of an ingrowth surface in an implantable device.

Figure 21B:
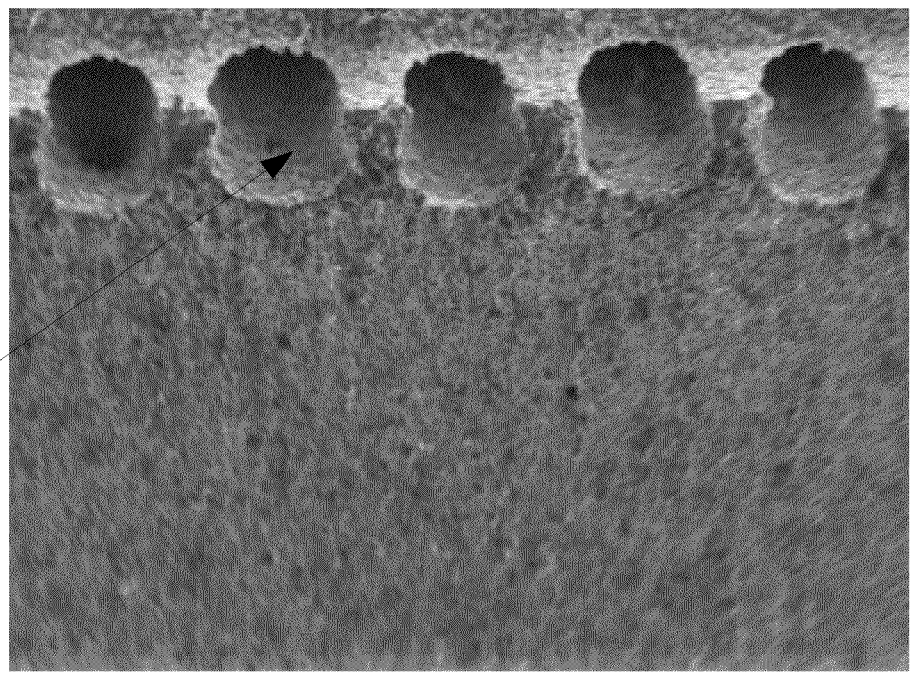

FIG. 21b is an image of the interface surface of an article molded with the monolithic insert of FIG. 21.

Figure 22:
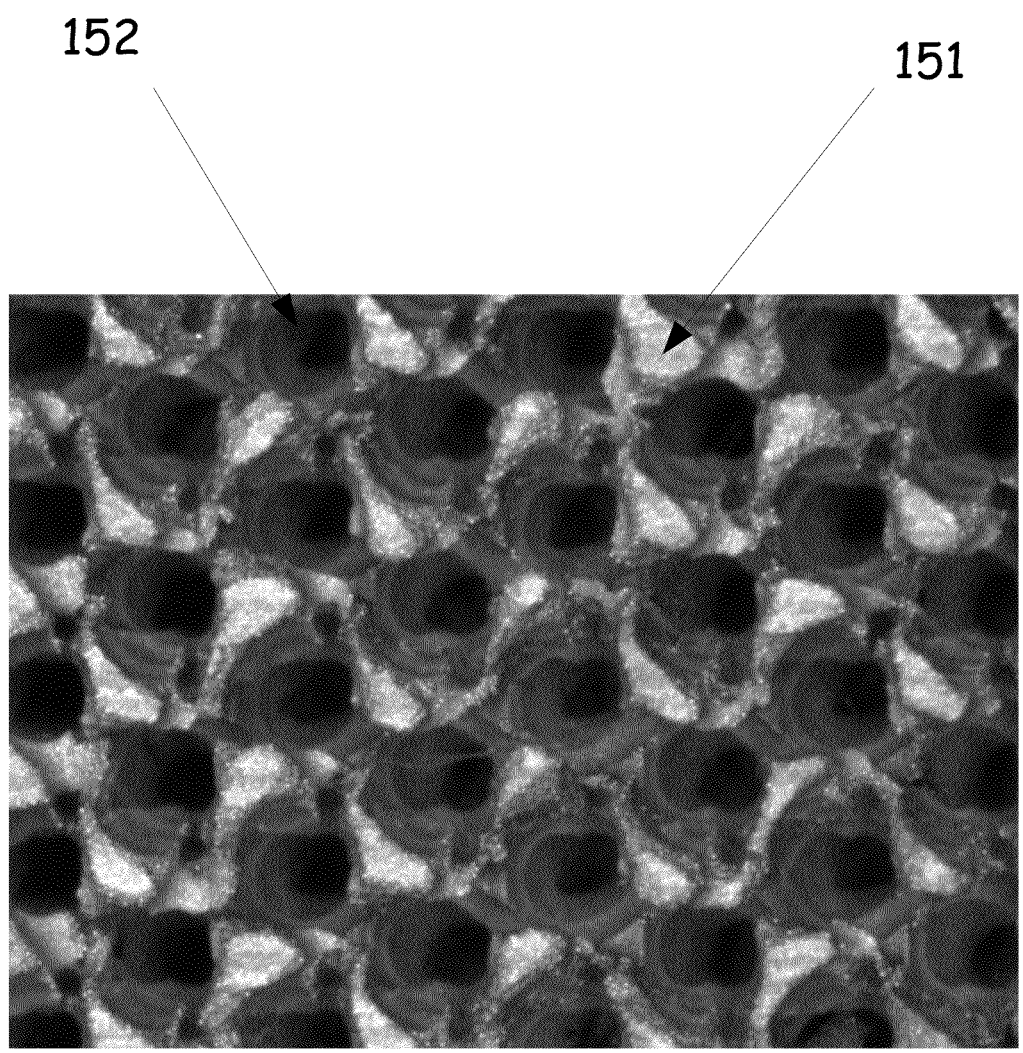

FIG. 22 is an enlarged view of the surface texture and ingrowth surface of an implantable device according to an embodiment of this invention.

Figure 23:
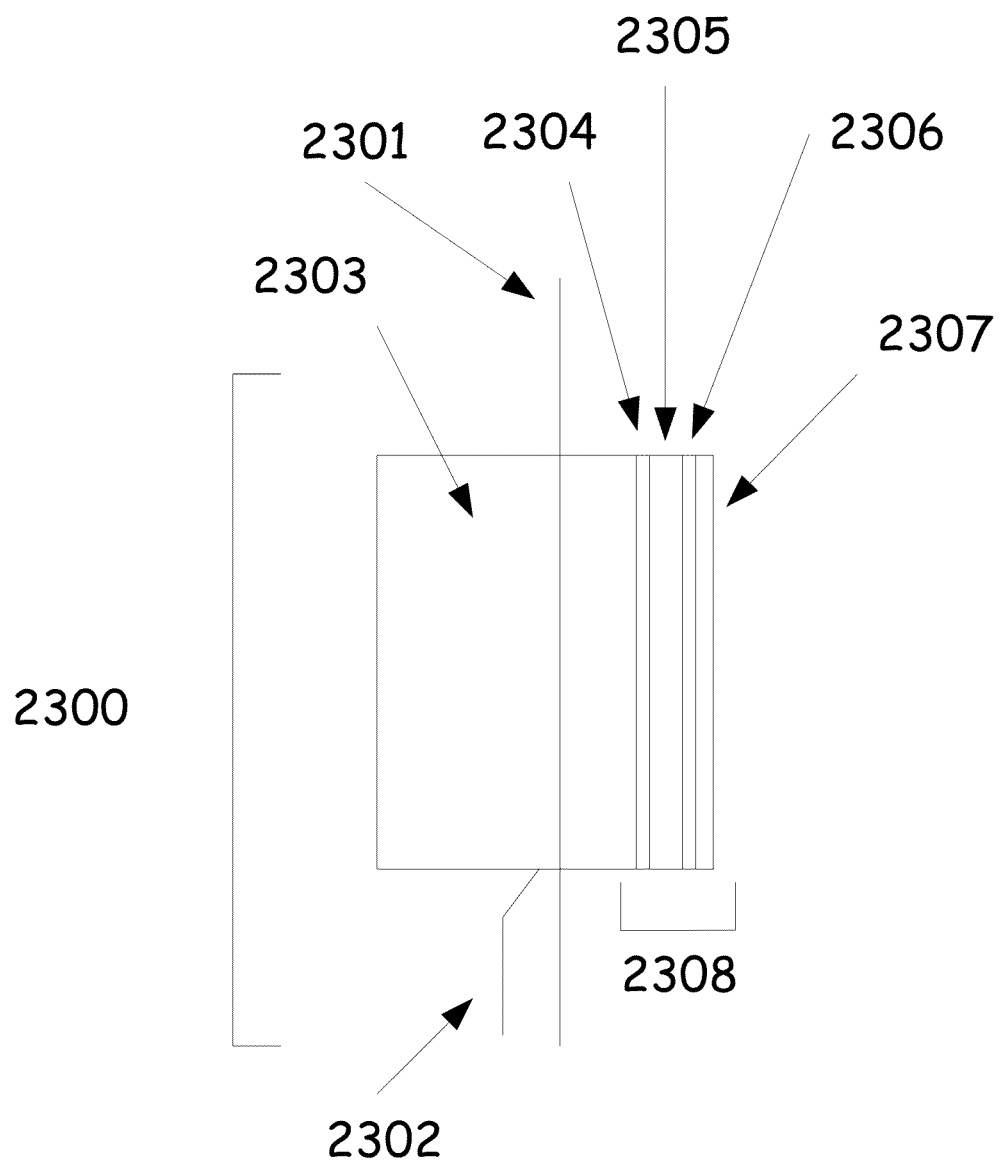

FIG. 23 is a schematic side view of a mold cavity with a monolithic insert placed in the cavity.

DETAILED DESCRIPTION OF THE INVENTION

The present invention relates to complex textured implantable devices manufactured by powder metal formation using precision monolithic mold inserts. The invention allows metal injection molding to be used to form implantable devices incorporating a high strength textured portion where at least a portion of the surface of the device is entirely defined by a monolithic mold insert.

By using the present invention, load bearing implants having a complex textured characteristic and high strength are manufactured using a metal injection molding process with sacrificial mold insert. Implantable devices manufactured by powder metal injection molding having porous and non-porous regions are enabled having a static tensile strength (or tensile bond strength) of the textured region of 20 mega Pascal (MPa) or greater. The powder metal maybe selected from a wide range of known biocompatible metals. In preferred embodiments, either commercially pure titanium or Ti-6Al-4V alloy powders are used.

The process according to the present invention provides for implantable devices having a textured portion defined entirely by a complex mold insert. The insert is engineered to have specific texture and surface properties to achieve the desired properties in a molded article, including reducing the stress concentrators and optimizing strut geometry, as well as material usage. Implantable devices having porosities ranging between 40 and 90 percent porous have been manufactured using monolithic mold inserts according to the present invention. Along with the ability to control the porosity, the present invention provides for the bulk modulus of the ingrowth medium to be varied, thereby enabling full control over the various regions of the implantable device.

In terms of the present invention, the monolithic mold insert is used to form a textured portion of the device, which may include one or more of the following regions: The fixation region which refers to the portion of an implant that generally provides for initial fixation of the device during surgery; the ingrowth region which is the portion of an implantable device that is intended to promote growth of tissue into the device for long-term fixation; and the substrate interface region which is the transitional area between the textured portion and the dense portion of the implant.

According to the present invention, the use of metal injection molding together with sacrificial monolithic inserts formed by additive manufacturing provides implantable devices having an improved tensile bond strength of the textured portion of 20 Mega Pascal.

The use of sacrificial monolithic inserts with metal injection molding according to the present invention provides for design and control over three critical aspects of the textured portion on implantable devices: (1) the fixation region, (2) the ingrowth region, and (3) the interface region as further discussed below.

Figure 1:
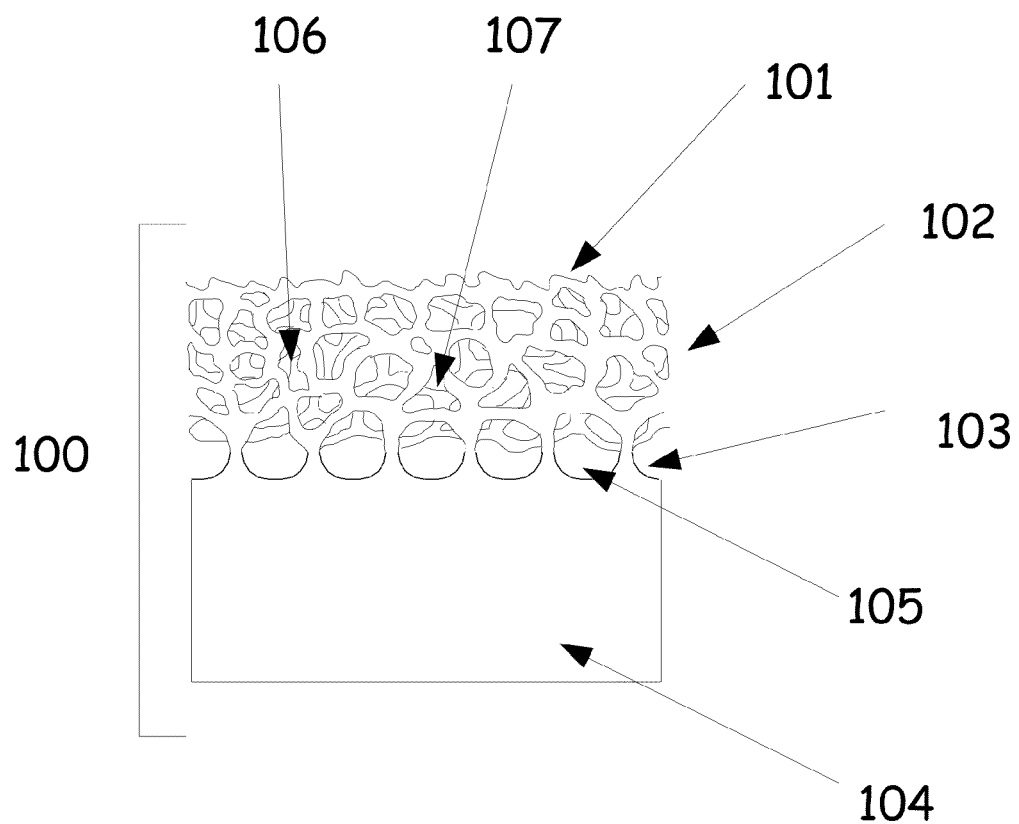
FIG. 1 illustrates a schematic cross-sectional view of an embodiment of a implantable device having a textured portion.

FIG. 1 shows a schematic illustration of an implantable device 100 in accordance with the present invention. The textured portion includes the fixation region 101, the ingrowth region 102, and the substrate interface region 103. As shown in FIG. 1, the ingrowth region 102 is separate and can have distinct properties from both the fixation region 101 and the substrate interface region 103.

The textured portion according to the present invention, may have one or more of the following characteristics: A portion with interconnected porosity, a porous biocompatible metal material having a porosity (preferably between 60 and 85 percent), an interconnected porosity where the average size of the interconnecting pores is preferably between 30 and 350 microns, and the major pore diameter is preferably between 100 and 700 microns. The pore characteristics may include random sized spherical pores 105, bimodal distribution of spherical pores, oblong, elongated pores 106 or polyhedral pores 107.

Figure 2:
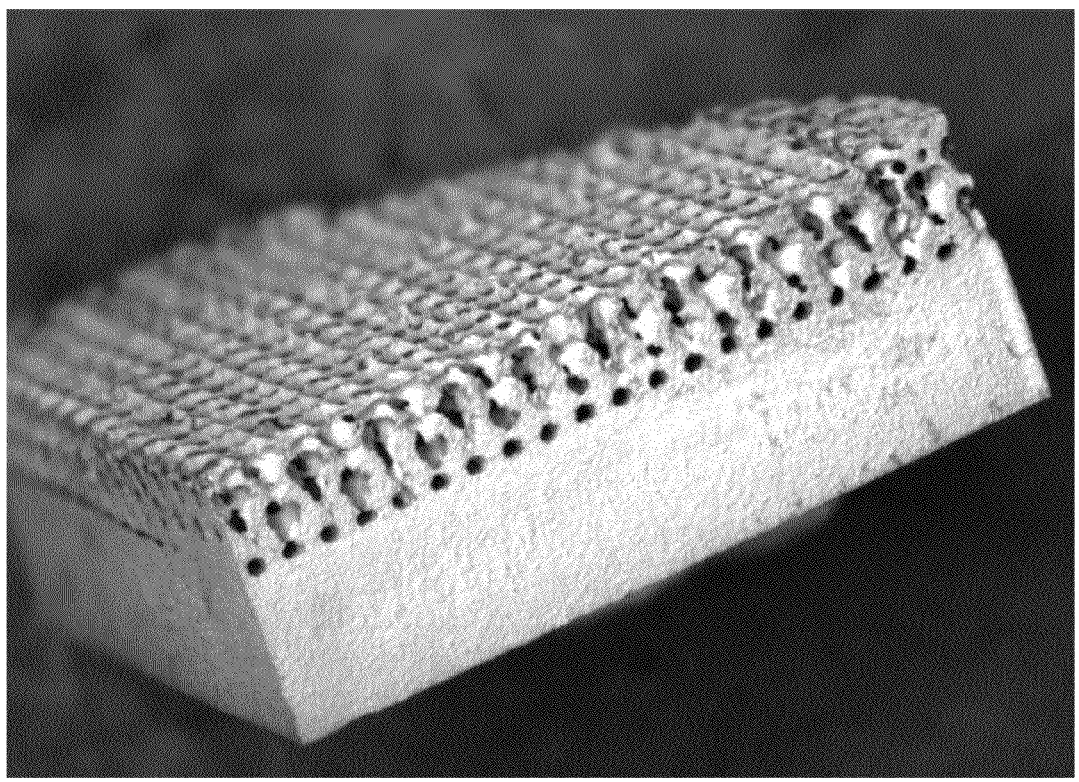
FIG. 2 shows a cross section of a high strength titanium article with a textured portion made using a sacrificial mold insert.
Figure 3:
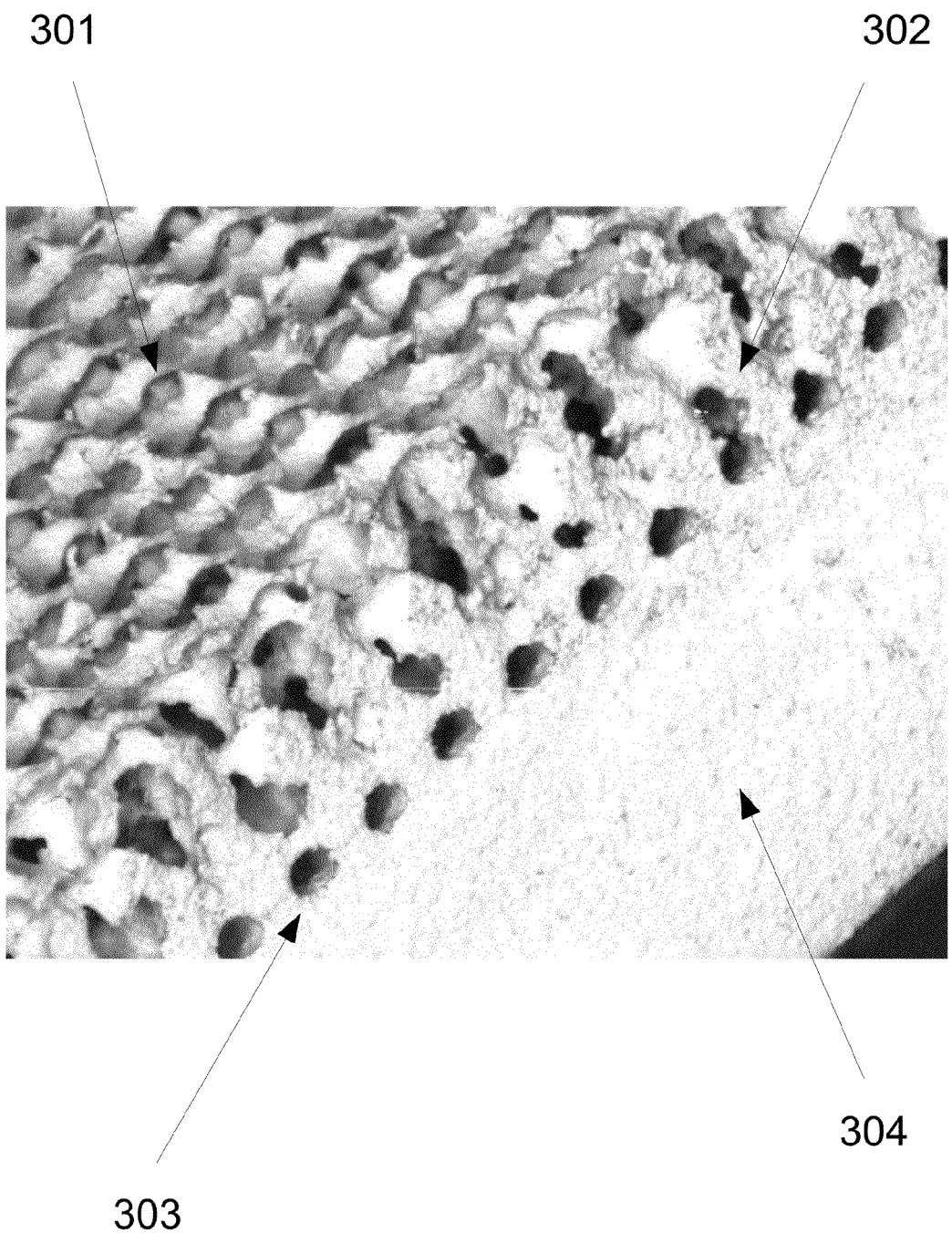
FIG. 3 shows textured regions on an implantable device according to an embodiment of the present invention.

FIG. 2 shows a cross section of a titanium article made using a sacrificial insert according to the present invention. FIG. 3 is a magnified view of the article of FIG. 2 and exemplifies the various regions according to the present invention, including the fixation region 301, the porous ingrowth region 302, and the substrate interface region 303, as well as the dense substrate 304 of the implantable device.

According to the present invention, the AM process has criteria particularly suitable in the formation of monolithic mold inserts for high strength textured devices made by metal injection molding, including a fixation region, and in growth region and an interface region.

Additive manufacturing technology is generally known as a process for making three dimensional solid objects of virtually any shape from a digital model. An additive process is used to deposit or print successive layers of material in different shapes. Examples of AM including stereolithography, three dimensional printing and other techniques allow the building of complex articles without tooling.

There are many different additive manufacturing technologies that can be used to make inserts according to the present invention. Three common AM approaches include Liquid Polymer Systems, Discrete Particle Systems, and Molten Material Systems. Similar methods using computer-controlled three-dimensional printing techniques can be used to build a mold insert having the desired textured portion. In accordance with the present invention, AM processes are used to manufacture mold inserts with textured portions such as undercut edges, pores, and other complex features.

Liquid polymer systems are known to form a solid object by curing or cross-linking a liquid polymer or polymer precursor, typically but not exclusively, with a photo-curing mechanism. In one embodiment, water soluble photopolymers are used to form water soluble inserts for dissolution after the article is injection molded.

Discrete particle systems are known to bond or fuse particle together to form a solid object. This may be done using successive layers of particles, and in complex, interconnected surface. Afterwards, unbonded powder from inside the insert can be removed by compressed air, ultrasonic agitation or other methods.

Molten material systems are known to form a solid object by applying a thermoplastic material through a delivery system similar to an extruder, and the part is built up layer by layer. Inserts can be fabricated, insert molded and removed to create texture, porosity or other complex surfaces. The most common of the commercially available methods is Fused Deposition Modeling (FDM).

Many polymer materials can be used as an insert material. Preferred embodiment materials are acrylonitrile butadiene styrene (ABS), ABS-like materials, and styrene and acrylic materials and other materials having similar thermal and solubility characteristics. These materials lend themselves to FDM techniques and are readily available.

The present invention includes the use of AM to manufacture monolithic inserts for metal injection molding, where the inserts include shapes for the formation of the desired undercuts, internal cavities, hollow areas, and/or voids. For simplicity, such textures on a molded article that do not release from a mold insert after injection molding due to their geometry shall be comprehensively referred to as "complex texture" or "undercuts" herein. Such features can include but are not limited to bridges, ridges, hooks, tunnels and pores. AM can be used to create sacrificial inserts that can impart complex texture and porosity to a molded article. Moreover, the AM inserts can be removed after molding by dissolution or decomposition. The material should be readily removed from the injection molded article without leaving behind residual material that could contaminate the molded article. This can be achieved primarily by dissolving the insert or thermally decomposing the insert. In a preferred embodiment, the insert is removed before thermal debinding. Liquid may be used to extract the first phase of the MIM binder prior to thermal debinding. This liquid can be water or a solvent and ideally the insert material can be chosen to be removed using the same solvent. Removing the insert prior to thermal debinding ensures that the insert does not contaminate the finished article. Some MIM systems use a first phase that is catalytically decomposed at low temperature; the insert material can be selected to be compatible with this type of process as well.

According to the invention, the material used for the monolithic AM insert should withstand the temperature and pressure of the molten metal injection molding feedstock. Materials such as cellulose based resins are good candidates for AM inserts because they readily satisfy the requirement of withstanding temperature and pressure of injection molding, yet can be selected to be readily soluble in water or organic solvents. Material blends such as a metal salt with a binder can be manufactured by AM as inserts.

After molding, the insert is removed without compromising the strength and other physical properties of the textured implantable device. The removal step can be a discrete, additional step or it can be incorporated into a typical first stage debinding step used in for the metal injection molding manufacturing process. Such debinding can include solvent or water immersion or acid debinding. It may be desirable to make the insert out of a material that is compatible with the first stage debinding step or it may be advantageous to remove it in a separate step. The flexibility of the AM process allows for a selection of the ideal material for the sacrificial insert based on the best debinding operation. According to the present invention, removal of the insert after molding of the device can be accomplished by thermal or solvent debinding or by solvent extraction.

Because additive manufacturing creates monolithic mold inserts that define all features of a region of an implantable device in the negative of the desired texture, secondary operations are minimized or avoided entirely after the material is formed. In addition to the streamlining of manufacture this allows very specific tailoring of the outer surface texture. In addition, the present invention allows for control over surface textures, interconnected porosity properties, including interconnected pore diameter, major pore diameter and a reduction of stress concentrators.

The invention allows further for the control over the individual characteristics of each pore former as well as the fusing and/or interconnection of the pore formers. According to one embodiment of the instant method, pore formers are fused to their adjacent pore formers as they are formed. This allows for direct control of the nature of the interconnection between pores in the molded implantable device.

The use of fused pore formers by AM on a monolithic insert overcomes several of the limitation of discrete pore formers. Fusing of the pore former allows more control over the nature of the final porous article. For example, the maximum porosity of an article formed using discrete pore formers is limited by the packing density of pore formers. Fused pore formers in monolithic inserts are used to produce porous material over 80 percent porous according to the present invention. Moreover, a titanium device with a 70 percent porous region made using an insert for metal injection molding according to the present invention with fused pore formers has a tensile bond strength of 64 MPa.

Interconnecting porosity is a critical attribute in many porous applications. In orthopedics, the interconnecting pores must be above a certain minimum in order to allow ingrowth of bone. As discussed previously, the interconnecting porosity in an article fabricated using discrete pore formers is created by pore formers contacting each other during the forming process. In a compaction scenario, the pore formers contact each other and then deform slightly against each other to form the interconnecting porosity. The contact area between pore formers dictates the size of the porosity between adjacent pores. In systems using a discrete pore former several variables affect the final interconnecting pore size. Among these variables are the compressibility of the pore former, the packing density of the pore former and the amount of metal powder included in the mixture.

Fusing the pore formers not only overcomes the limitations of particle packing density in the porous material, but decouples the size of the interconnecting porosity from the specific characteristics of the discrete pore formers. Using fused pore formers allows very specific control over the connection between the pores.

Figure 4:
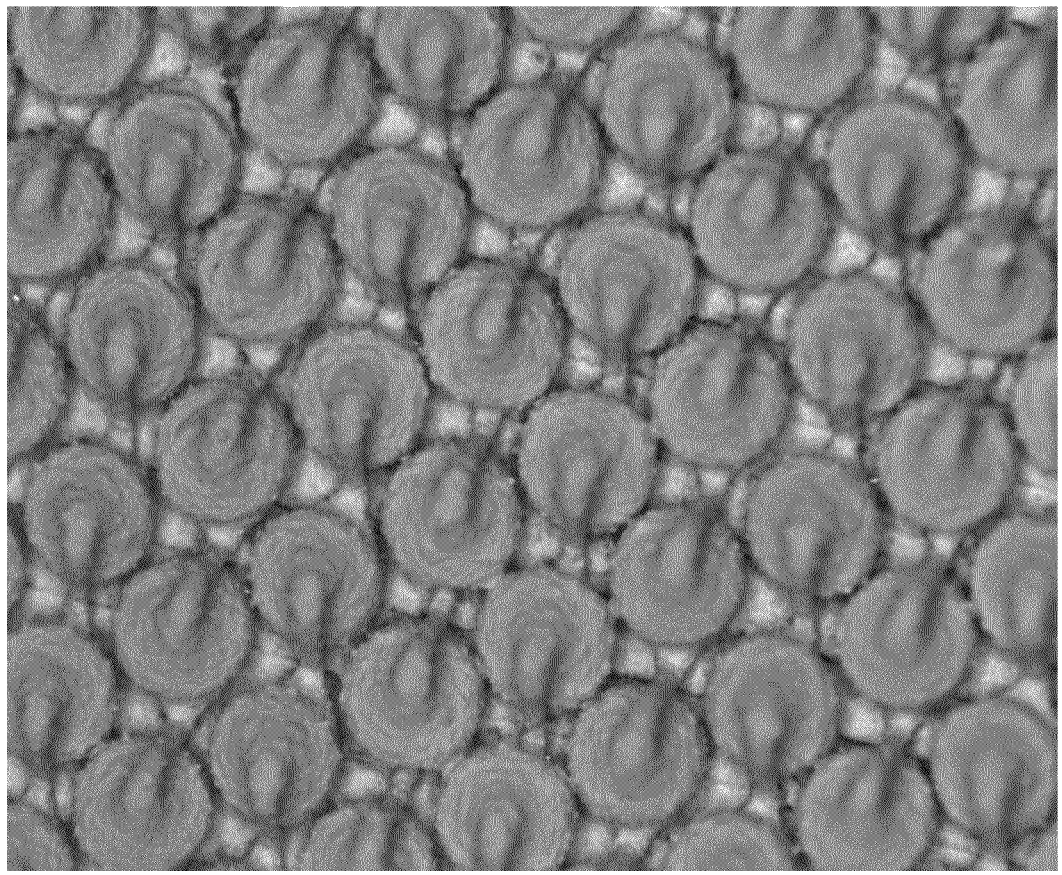
FIG. 4 and FIG. 4a illustrate fused pore formers on a monolithic insert for forming the interconnecting porosity.
Figure 4A:
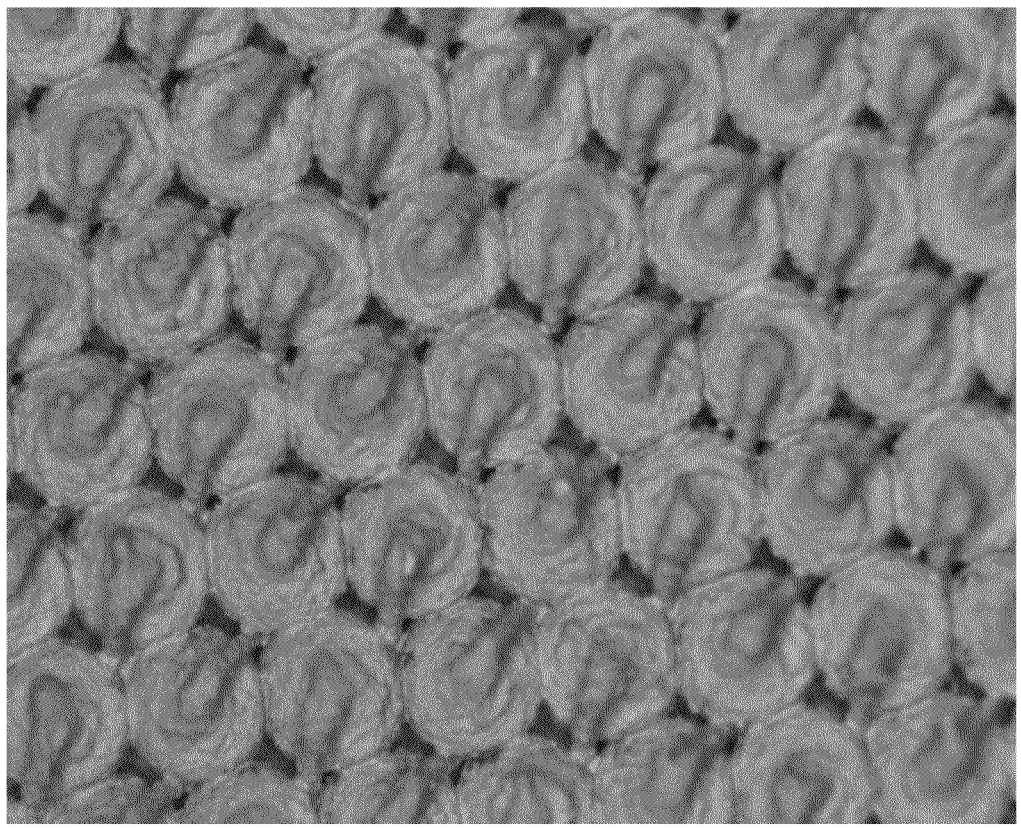

FIG. 4 illustrates various embodiments of using fused pore formers to control the interconnecting porosity. Many other structures of the pore formers can be created to meet the requirements of the specific implantable device. The pore formers can be placed farther apart without contact in between the pore formers or so close together that they do not allow the matrix material to flow between them.

In a preferred embodiment, the additively manufactured monolithic insert is secured in the mold by means of a portion of the insert that extends past the mold cavity or volume of the molded part. This may manifest itself as an extension of the depth of the insert, or by the addition of tabs or features to the insert which are used to secure it in the mold. Elements such as holes or bosses can also be used to secure the insert in the mold.

Referring to FIG. 23 the schematic depicts the side view of a mold 2300 with an insert 2308 placed in the cavity 2303. Feedstock material enters the cavity via the runner and gate 2302. The parting line 2301 of the mold indicates the place where the mold opens after the injection process is complete. The insert 2308 has several layers and is in contact with the mold 2300 by layer 2307. The fixation texture is defined by layer 2306. The porous ingrowth section 2305 of the insert defines the specific nature of the porosity and the innermost layer 2304 defines the interface between the porous section and the solid section of the molded article.

Certain embodiments may not use porosity, but rely on a rough surface rather than interconnected porosity to create osseointegration. The AM inserts allow the tailoring of the size of the elements of which the roughness is composed, the spacing between those elements and the overall density of the medium. Since the advantages of the invention can be applied to any type of ingrowth surface, the inventions includes all surfaces intended to integrate with hard or soft tissue.

The nature of the ingrowth region is defined by the electronic model or program used to generate the additively manufactured insert. Because additive manufacturing does not require tooling to manufacture the insert, the design criteria are not limited by conventional limitations such as the requirement to have the insert capable of being released from tooling. Because there are no discrete pore formers, the shape of the pore is can be shaped as desired by the AM insert.

According to the present invention, using AM to form a sacrificial monolithic insert for the purpose of forming high strength textured devices allows for the nature of the fixation region to be tailored independently of the nature of the ingrowth region and the interface region, while forming an insert with reduced stress concentrators.

Figure 5:
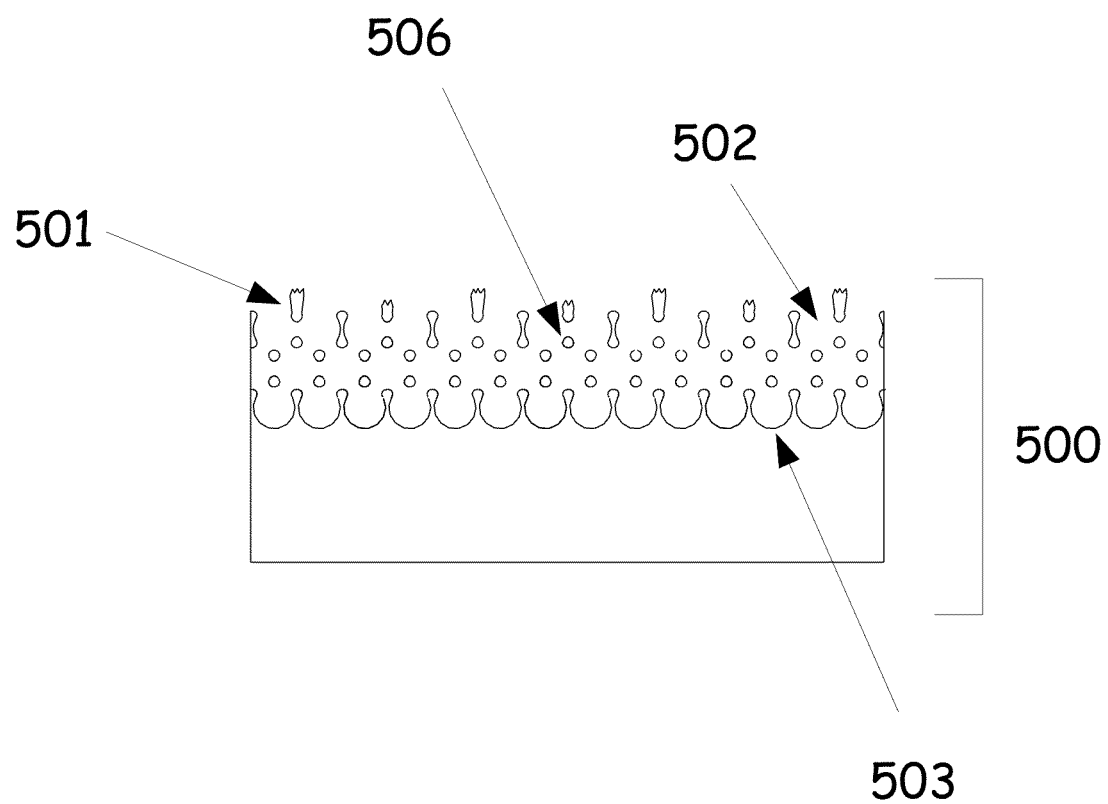
FIG. 5 and FIG. 5a are schematic views illustrating a section of an ingrowth region of an implantable device having reduced stress concentrators in the interface region.
Figure 5A:
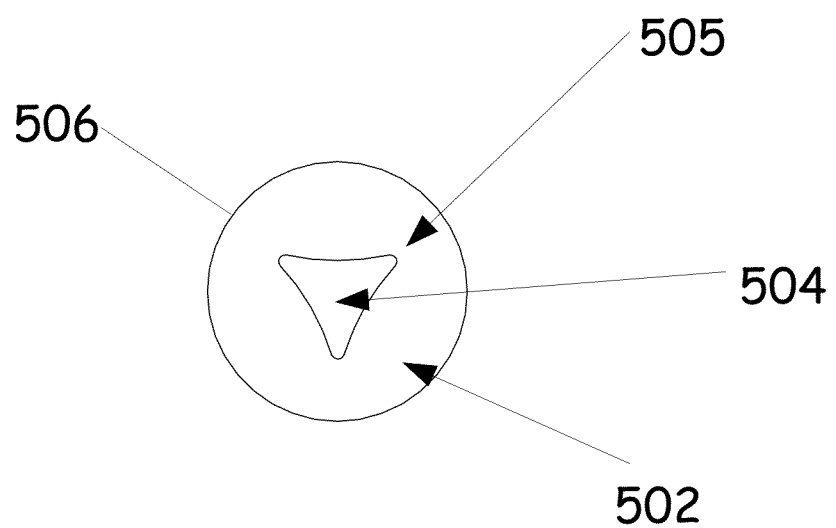

FIG. 5 is a schematic representation of a cross-sectional slice of one embodiment of a device 500 having an interface portion 503 according to one embodiment of the present invention. FIG. 5 illustrates an ingrowth medium in which the cross-sectional geometry of the struts 504 is optimized to reduce stress concentrators. The textured portion includes the fixation region 501, the ingrowth medium region 502, and the interface region 503. FIG. 5A is a magnified view of 504 and shows a cross-section of the structural metal of the ingrowth medium 502 that has rounded edges 505 formed by the engineered AM insert according to the present invention. The round edge 505 connecting the pores or open areas 502 is engineered to reduce the stress concentration in the struts in accordance with the present invention.

Figure 6:
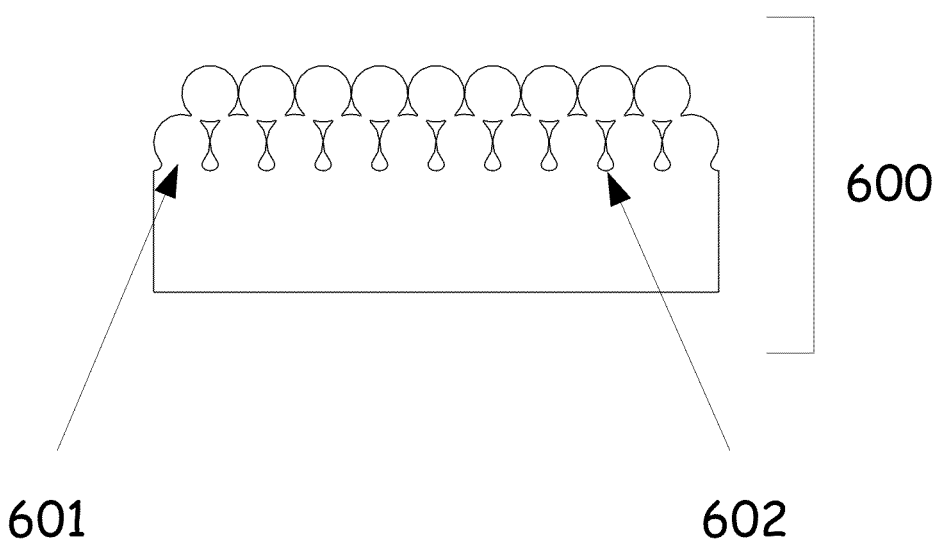
FIG. 6 illustrates a schematic cross-section of a beaded surface of a texture portion of implantable devices.

FIG. 6 illustrates a schematic representation of a cross-section of a beaded surface used as another embodiment of the textured portion on implantable devices. A conventional surface forms a point bond on the surface at the contact between the bead and the substrate. The use of AM to form a sacrificial insert in conjunction with metal injection molding according to the invention enables the optimization of the substrate interface 601. The contact area between the beads and the substrate has been greatly increased, which increases the tensile bond strength between the texture and the substrate. In one embodiment, point disruptions on the surface, which act as stress concentrators, have been designed to include smooth curves 602 rather than points. Reduction of these stress concentrators improves the fatigue life of the textured device.

According to the present invention, the surface of the implantable device manufactured by metal injection molding to a specific geometry designed by the monolithic AM insert. The device has a high tensile bond strength (TBS) of the textured portion on the devices. A sample implantable device with a 80% porous textured portion according to the present invention has been shown to have a TBS of 80 MPa for the porous portion. For this sample, the pore forming elements of the monolithic mold insert were stacked rods with alternating orientations.

The TBS of the porous region in the molded device varies with the shape of the pore formers, as well as the porosity. TBS for the porous region of test samples is shown below in Table I, including the type of monolithic mold insert used for metal injection molding:

TABLE I

| Monolithic Insert | Porosity (%) | Tensile Strength (MPa) |
| --- | --- | --- |
| Fused Pore Former, Spheres | 70 | 64 |
| Fused Pore Former, Rods | 80 | 80 |

In another example, the formed surface was subjected to tensile bond testing and demonstrated tensile bond strengths in excess of 50 MPa at 70% porosity. The major pore diameter is approximately 500 microns and the minor pore diameter is above 100 microns.

Figure 7:
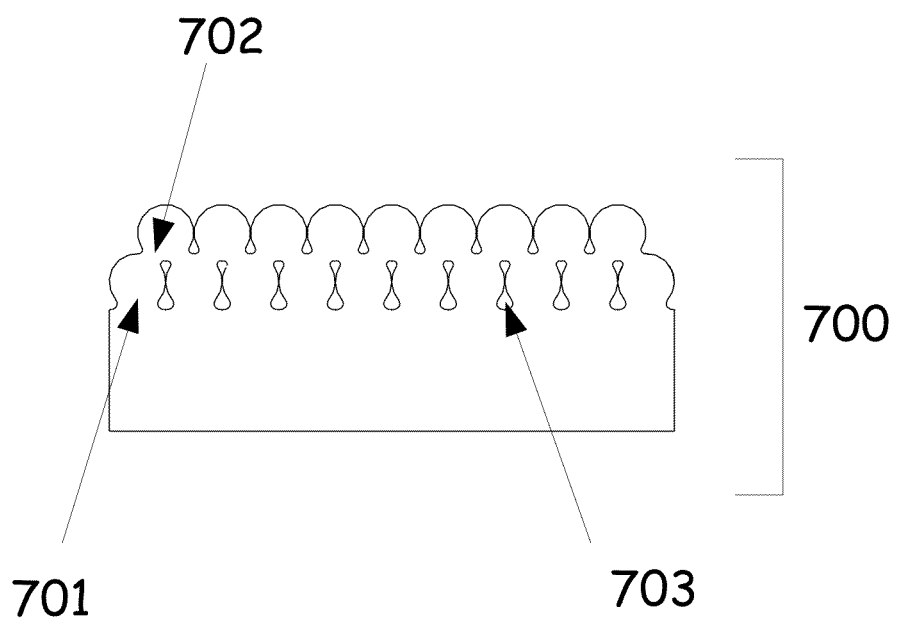
FIG. 7 is a schematic cross-section of a beaded surface of a textured portion of an implantable device with increased contact area between the beads as well as increased contact area between beaded textured portion and the substantially dense portion.

FIG. 7 shows a schematic of an embodiment according to the present invention having a ingrowth medium 703 including the substrate interface 701. By increasing the contact area 702 between the beaded elements, the bulk strength of ingrowth medium is increased.

In another embodiment, the texture of the present invention includes interruptions of the surface. Interrupting the surface of a porous material creates a feeling of texture. This interruption can take many forms, such as grooves, peaks and valleys or trenches, as well as more random elements that also provide a more organic appearance.

Surface texture region can be created according to the present invention to appear more organic (like cancellous bone) which can enhance fixation. More organic surfaces can be created by incorporating algorithms into the AM program to represent the desired surface of the insert. FIG. 8 shows a surface made with a regular, repeating pore array. FIG. 8a shows a surface that was molded with a complex insert to appear less regular and more random or organic to represent cancellous bone. FIG. 8b is a photograph of the device having the surface shown in in FIG. 8a.

Using AM, an array can be used for the highly repeatable generation of surfaces having an organic appearance. Many different algorithms or mathematical approaches could be used to effect similar disruption of the surfaces appearance, including, for example, an array based on Penrose tiling.

As schematically shown in FIG. 9, the fixation region of the present invention includes "Porcupine" elements such as fine protrusions and recessions that are designed into the surface. In another embodiment, the texture of the present invention includes barbs or fish scale elements: Elements such as this allow the surface to pass easily in one direction but resist movement in another.

In an alternative embodiment, all or a portion of the insert made by AM are filled by injection molding and then placed into another mold cavity and molded against to incorporate the prefilled insert into a larger part. This is particularly applicable to address difficulties in filling the insert or the challenges of molding both large section and detailed sections. Alternatively it can be used to combine molding technologies. For instance, the monolithic insert is prefilled using a high pressure injection route and the larger molded body into which the prefilled insert is incorporated is molded using low pressure injection.

In another embodiment, the invention to form mechanical features in addition to the textured portion. For example, a porous thread or boss can be created in this manner; the insert is designed to form the mechanical feature as well as the textured portion.

According to an embodiment of this invention, the insert has a melting point or Heat Deflection Temperature (HDT) at or below the melt processing range. Typical melt temperatures of MIM feedstock are in the 155-185° C. range. Materials with a heat deflection temperature lower than the feedstock temperature can be used to form textured and porous surfaces. For example, an acrylic based thermoplastic material with a HDT of less than 90° C. is used as an insert material. The insert is fabricated by Fused Deposition Modeling (FDM), an additive manufacturing technique known in the art. The insert is placed in the injection molding tool and MIM feedstock is molded against it. The insert does not exhibit significant deformation from the heat and pressure of the molding operation.

According to the present invention, materials with a melting point substantially lower than the injection molding melt temperature can be used to form the insert. As another example, inserts were fabricated from acrylonitrile butadiene styrene (ABS), having a melting point of 105° C., and MIM feedstock having an injection molding temperature of 165° C. was molded against the insert. Subsequently, the insert was removed via solvent immersion. The use of lower HDT materials for the insert presents benefits in the manufacture of the insert and the processing of the molded article. Materials with lower melting points are easier to process via Fused Deposition Modeling and require less complicated equipment. Higher temperature materials require more specialized equipment and present challenges in melting, extruding and controlling deformation of the insert during cooling. Lower melting point materials are also generally easier to remove by virtue of being more readily soluble at lower temperatures.

FIG. 10 illustrates a porous section adjacent to a solid section formed by injection molding MIM feedstock into and against a soluble monolithic insert. FIG. 10a shows a close up of the textured portion, the metal of the finished article is continuous throughout the article with a structure of the porous and the solid section. The pore diameter shown is approximately 300 microns.

FIG. 11 show two test disks made with differing porosity. 1101 has an ingrowth region that is 80 percent porous and 1102 has an ingrowth region that is 45 percent porous.

Another feature of the present invention is the ability to replicate preexisting textured portions such as those of natural bone. Desired textures can be scanned with any number of conventional surface scanning technologies and the resulting digital file used to create a monolithic insert by AM. The insert is placed in a mold and the device is injection molded.

According to the present invention, the scanned image can also be modified to add desirable characteristics such as geometries in the valleys of the roughness that reduce stress concentrations or remove undesirable characteristics and increase the fatigue strength.

FIG. 12 shows a textured surface region that was replicated form a scanned sample that was scanned with a three dimensional scanner and converted into a negative of the sample to create a monolithic insert surface. The resulting surface was printed using a FDM type machine to form the insert, and then injection molded against.

Referring to FIG. 13, the schematic 1300 depicts the surface of the device shown in FIG. 12. The interface of the textured portion and the dense portions can be modified to increase fatigue strength by reducing abrupt changes at the interface 1301. The interface 1301 of the fixation portion 1302 is rounded to smooth the transition between the textured portion and the substrate material.

The present invention may also be used to manufacture implantable devices that include an integral bearing or wear material. In certain applications, it may be desirable to affix a polymeric wear material on a device. Devices such as these are often referred to as having a unitized or monoblock design where the polymeric bearing material is molded, formed or otherwise affixed directly against the metal implant body.

According to the present invention, the insert for monoblock devices includes a fixation or anchoring surface intended for the bearing or wear material. With certain implantable devices such as acetabular cups, the metal portion may be a bone ingrowth medium formed by an AM insert according to the present invention and connected directly to the polymeric wear material, with little structural aspect to the metal portion of the cup. By virtue of the design of the insert, the molded article may comprise a biological integration layer, and anchoring surface for the bearing material and a barrier between the two.

With this in mind it is desirable to create a surface on the metal body with a molding insert which the plastic bearing material can be formed against, thus allowing the plastic to form a strong mechanical bond between the molded plastic section and the metal. Surfaces with undercuts, cavities, and notches below the surface are used to form these types of bonds.

The polymer anchoring layers formed according to the present invention can be tailored based on the requirements of the device. One embodiment is an interlocking layer that allows polymer bearing material to be molded into and around it. FIG. 14 illustrates an example of this type of surface, where the interlocking layer is approximately 0.024 inches thick.

A cross-section of the molded article incorporating an interlocking style of anchoring surfaces is shown in FIG. 16. This interlocking surface used was similar to the surface depicted in FIG. 14. FIG. 15 shows a schematic of an undercut layer. The undercuts formed by the monolithic insert in the metal surface portion of the device is shown in 1603. The polymer material 1602 was molded through the interlocking surface and against the metal substrate 1603. The interlocking surface formed allows for a strong bond between the polymer material 1602 and the metal substrate undercuts 1603.

The mechanical properties of both interlocking surfaces and undercut surfaces as an anchoring surface for the polymer material are very high. The undercut surfaces had an average tensile strength of 14 Mega Pascal for the polymer and the interlocking surfaces had an average tensile strength of 17 Mega Pascal for the polymer.

Other types of surfaces can also be used. Molding against single filaments, or rod like features, creates a surface with many undercuts on it as shown in FIG. 15. These undercuts also interlock with the polymer material and are useful in reducing the overall thickness of the anchoring layer. In one embodiment, this layer is approximately 0.014 inches thick and formed using Fused Deposition Modeling by extruding a very fine deposition of plastic and building it up with multiple depositions.

FIG. 17 shows a schematic of a monoblock tibial tray construction with an interlocking surface formed on the tray during the MIM process. FIG. 17 shows one embodiment using an insert of two layers of cylinders to create the interlocking texture. FIG. 18 shows a schematic of insert used to form the interlocking surface of FIG. 17. The surface 1801 is defined entirely by the insert during molding such that when the MIM feedstock is injected it does not come in contact with the tool steel of the mold behind the insert. This allows for a surface that has a highly desirable interlocking nature formed by the filament pore formers 1802 of the insert.

Using the AM process for making a monolithic insert, functional sections of the insert may be fabricated simultaneously or sequentially, depending on the geometry of the desired insert. FIGS. 19, 20 and 21 depict portions of inserts manufactured by AM according to the present invention for the fixation region, ingrowth medium region and substrate interface region of an implantable device, respectively.

FIG. 19 is a photograph of an insert fabricated by AM used to form a fixation region similar to the texture depicted in FIG. 12. FIG. 19a is a magnification of the insert surface. FIG. 20 is a photograph of a monolithic insert fabricated by AM used to form an ingrowth region according to the present invention. An array of beads is printed in such a fashion as to provide connection between the beads and consequently between the pores which are left after the insert has been molded into and removed. FIG. 20a and FIG. 20b are successive magnifications of the insert in FIG. 20. In FIG. 20b the connection 2001 between the beads will form an interconnecting pore in the final article and the space 2002 between the beads will form metal struts of the ingrowth medium.

FIG. 21 is a photograph of an AM fabricated monolithic insert used to form the substrate interface according to the present invention. FIG. 21a is a magnification of FIG. 21. The strands 2101 that run diagonally will form the rounded interface between the ingrowth medium and the substrate or dense section. 2101 are on top of the bead elements 2102 creating the ingrowth medium. FIG. 21b is a cross-sectional photo of a part that was metal injection molded using an AM manufactured insert of FIG. 21 to form the substrate interface. The rounded interface 2103 forms a smooth transition between the ingrowth region and the substrate or dense section.

FIG. 22 shows a magnified view of a portion of a sintered implantable device according to present invention. The surface region 2201 and ingrowth region 2202 are formed by an AM insert.

In another embodiment, it is desirable to manufacture the implant using two or more different metal materials. For example, the texture formed by the AM insert can be of a different material than the substrate of the implant.

In one embodiment, the material used in the porous section is desired to be different that the material used in the solids section this can be accomplished by first injecting feedstock into the monolithic insert, without forming the bulk of the solid section and then injecting the desired bulk alloy around the previously filled insert. Alternately, the sequence of forming could be reversed.

In another embodiment, secondary operations can be used to improve the mechanical performance of the finished article. These may include mechanical or chemical finishing of the surface or heat or chemical treatment of the article to alter the microstructure of the article.

Although the present invention has been described in terms of examples and presently preferred embodiments, it is to be understood that such disclosure is not to be interpreted as limiting. Various alterations and modifications will no doubt become apparent to those skilled in the art after having read the above disclosure. Accordingly, it is intended that the claims be interpreted as covering all alterations and modifications as fall within the true spirit and scope of the invention. For example, the invention could be applied to ceramic materials and the field of ceramic injection molding.

What is claimed is:

1. A method of forming an implantable device or part thereof, such method comprising the steps of:
   blending a binder and a first powder of metal particles to form a first homogeneous mixture;
   forming a monolithic mold insert by an additive process, wherein the insert has a complex texture;
   placing the mold insert in a mold;
   injection molding the first homogeneous mixture into the mold and the mold insert to form an article, wherein the mold insert forms a textured portion in the article;

removing the article and the insert from the mold;
removing the insert from the article; and
sintering the article to form the implantable device or part thereof, the implantable device or part thereof having interconnected subsurface porosity.

2. The method of claim 1, wherein the complex texture comprises a fused pore forming region.

3. The method of claim 1, wherein the textured portion comprises an ingrowth region of the implantable device.

4. The method of claim 3, wherein the ingrowth region has an interconnected porosity of at least 45 percent.

5. The method of claim 3, wherein the textured portion further comprises a fixation region.

6. The method of claim 5, wherein the textured portion further comprises an interface region to a dense portion of the implantable device.

7. The method of claim 5, wherein the fixation region has undercuts.

8. The method of claim 1, further comprising blending a binder and a second powder of metal particles to form a second homogenous mixture and injection molding said second mixture after said step of injection molding the first mixture.

9. The method of claim 1, wherein the first powder metal is selected from the group consisting of commercially pure titanium and titanium alloy.

10. The method of claim 1, wherein the textured portion has a tensile bond strenghth of 20 Mega Pascal or greater.

11. The method of claim 1, wherein the additive process is a liquid polymer system.

12. A method of forming a textured portion of an implantable device, such method comprising the steps of:

blending a binder and a powder of metal particles to form a homogeneous mixture;
forming a monolithic mold insert by an additive manufacturing process having a first surface for making contact with a mold and a second surface having a texture;
placing the insert in a mold such that the first surface is in contact with the mold;
injection molding the homogeneous mixture into the mold to form an article having a textured portion defined entirely by the second surface of the mold insert;
removing the article and the mold insert from the mold;
removing the insert so as to maintain the textured portion on the article; and
sintering the article to form the implantable device with the textured portion, the textured portion having interconnected subsurface porosity.

13. The method of claim 12, wherein the textured portion has tensile bond strength of 20 Mega Pascal or greater.

14. The method of claim 12, wherein the additive manufacturing process comprises three dimensional printing.

15. The method of claim 12, wherein the textured portion comprises the texture of cancellous bone.

16. The method of claim 12, wherein the textured portion comprises a fixation region, a porous ingrowth region, and an interface region.

17. The method of claim 16, wherein the ingrowth portion has porosity between 60 and 85 percent.

18. The method of claim 12, wherein the second surface having a texture comprises a fused pore former.

19. The method of claim 12, wherein the additive manufacturing process is a liquid polymer system.

* * * * *